(12) United States Patent
Mosher et al.

(10) Patent No.: US 6,869,939 B2
(45) Date of Patent: Mar. 22, 2005

(54) FORMULATIONS CONTAINING AMIODARONE AND SULFOALKYL ETHER CYCLODEXTRIN

(75) Inventors: Gerold L. Mosher, Kansas City, MO (US); Karen T. Johnson, Lawrence, KS (US); Atef A. Gayed, Overland Park, KS (US)

(73) Assignee: CyDex, Inc., Lenexa, KS (US)

( * ) Notice: Subject to any disclaimer, the term of this patent is extended or adjusted under 35 U.S.C. 154(b) by 0 days.

(21) Appl. No.: 10/139,620

(22) Filed: May 4, 2002

(65) Prior Publication Data

US 2003/0216353 A1 Nov. 20, 2003

(51) Int. Cl.[7] ..................... A61K 31/724; A61K 31/343
(52) U.S. Cl. .......................................... 514/58; 514/469
(58) Field of Search .................... 514/58, 469

(56) References Cited

U.S. PATENT DOCUMENTS

| | | | |
|---|---|---|---|
| 5,134,127 A | 7/1992 | Stella et al. | |
| 5,234,949 A | 8/1993 | Ehrenpreis et al. | |
| 5,376,645 A | 12/1994 | Stella et al. | |
| 5,874,418 A | * 2/1999 | Stella et al. | 514/58 |
| 6,046,177 A | 4/2000 | Stella et al. | 514/58 |
| 6,143,778 A | 11/2000 | Gautier et al. | |
| 6,204,256 B1 | 3/2001 | Shalaby et al. | 514/58 |
| 6,218,375 B1 | 4/2001 | Raghavan et al. | 514/58 |
| 6,267,985 B1 | 7/2001 | Chen et al. | |
| 6,294,192 B1 | 9/2001 | Patel et al. | |
| 2002/0012680 A1 | 1/2002 | Patel et al. | |

FOREIGN PATENT DOCUMENTS

| | | |
|---|---|---|
| WO | PCT/AU90/00418 | 4/1991 |
| WO | PCT/AU91/00071 | 9/1991 |

OTHER PUBLICATIONS

Okimoto, K. et al "The interaction of charged and uncharged drugs . . . " Pharm. Res. (1996) vol. 13, no 2, pp. 256–264.*

Leor, R. et al "The influence of pH on the intravenous delivery . . . " Eur. J. Clin. Pharmacol. (1990) vol. 39, pp. 521–523.*

Ward, Gary et al., Studies in Phlebitis VI: Dilution—Induced precipitation of Amiodarone HCI, Journal of Parenteral Science and Technology, vol. 47, No. 4, Jul.–Aug. 1993, 161–165.

Ravin, L.J. et al., Micelle Formation and Its Relationship to Solubility Behavior fo 2–Buty–3–benzofuranyl–4–[2–(diethylamino)ethoxy]–3,5–diiodophenyl Ketone Hydrochloride, Journal of Pharmaceutical Sciences, vol. 64, No. 11, Nov. 1975, 1830–1833.

Ravin, L.J., Effect of Polysorbate 80 on the Solubility and In Vivo Availability of 2–Butyl–3–benzofuranyl 4–[2–(Diethylamino)ethoxy]–3,5–diiodophenyl Ketone Hydrochloride.

* cited by examiner

*Primary Examiner*—Samuel Barts
*Assistant Examiner*—Leigh C. Maier
(74) *Attorney, Agent, or Firm*—Rick Matos; Innovar, L.L.C.

(57) ABSTRACT

The present invention provides aqueous parenteral formulations containing an antiarrhythmic agent, such as amiodarone, and a sulfoalkyl ether cyclodextrin. The liquid formulations are clear, sterilizable, and chemically and physically stable. The liquid formulations do not require a surfactant and do not precipitate upon dilution with distilled water or other pharmaceutically acceptable liquid carrier. The sulfoalkyl ether cyclodextrin-containing formulation provides significant advantages over other cyclodextrin-containing formulations of amiodarone. The formulation can be prepared in acidic, neutral and slightly basic medium while providing acceptable concentrations of amiodarone suitable for parenteral administration. An SAE-CD-containing formulation of amiodarone can be provided in liquid form or as a reconstitutable powder. Moreover, highly concentrated solutions exceeding 200 mg of amiodarone per mL can be prepared. Solutions can be made either dilutable or non-dilutable with water at room temperature or under conditions typically encountered in the clinic.

29 Claims, 5 Drawing Sheets

FORMULATIONS CONTAINING AMIODARONE AND SULFOALKYL ETHER CYCLODEXTRIN

FIELD OF THE INVENTION

The present invention relates to improved antiarrhythmic formulations and in particular to a parenteral formulation containing amiodarone and a sulfoalkyl ether cyclodextrin and to its use in the treatment of cardiac disorders.

BACKGROUND OF THE INVENTION

Antiarrhythmic drugs are commonly divided into four classes according to their electro-physiological mode of action (Edvardsson, Current Therapeutic Research, Vol. 28, No. 1 Supplement, pages 113S–118S (July 1980); Keefe et al, Drugs, Vol. 22, pages 363–400 (1981); Vaughn-Williams, "Classification of Anti-Arrhythmic Drugs in Symposium of Cardiac Arrhythmias", pages 449–472 (Sandoe et al, (eds.) A. B. Astra, Soederlaije, Sweden (1970)). Antiarrhythmic drugs are classified as follows: Class I—local anesthetic effect; Class II—beta-receptor blockade; Class III—prolongation of action potential duration; and Class IV—calcium antagonist.

Although it is generally considered a Class III antiarrhythmic drug, amiodarone possesses electrophysiologic characteristics of all four Vaughn-Williams classes: it blocks sodium channels at rapid pacing frequencies (Class I); it exerts a noncompetitive antisympathetic action (Class II); it prolongs the duration of the cardiac action potential (Class III); and it exhibits negative chronotropic effects on nodal tissues. Amiodarone possesses sustained efficacy against ventricular and supraventricular tachycardiarrhythmias. Amiodarone also exhibits vasodilatory action, which can decrease cardiac workload and consequently decrease myocardial oxygen consumption, and thus can be used to treat hypertension.

Amiodarone is approved for the treatment of life-threatening ventricular tachyarrhythmias. Amiodarone is also useful in treating less severe ventricular arrhythmias and many supraventricular arrhythmias including atrial fibrillation and reentrant tachyarrhythmias involving accessory pathways. Because amiodarone exhibits marked inter-individual variations in response, close monitoring of the individual is essential to adjust the amount of the drug delivered. The most important treatment-emergent adverse effects are hypotension, asystole/cardiac arrest/electromechanical dissociation (EMD), cardiogenic shock, congestive heart failure, bradycardia, liver function abnormalities, VT, and AV block (Wyeth-Ayerst product insert CORDARONE® Intravenous).

Amiodarone reportedly exhibits complex disposition characteristics after the intravenous administration of a single therapeutic dose. Peak serum concentrations after single 5 mg/kg 15-minute intravenous infusions in healthy subjects range between 5 and 41 mg/L. Peak serum concentrations after 10-minute infusions of 150 mg of CORD-ARON® I.V. in patients with ventricular fibrillation (VF) or hemodynamically unstable ventricular tachycardia (VT) range between 7 and 26 mg/L. Due to rapid distribution, serum concentrations decline to 10% peak values within 30 to 45 minutes after the end of the infusion.

Amiodarone HCl ((2-butyl-3-benzofuranyl)[4-[2-(diethylamino)ethoxy]-3,5-diiodophenyl]methanone hydrochloride; $C_{25}H_{29}I_2NO_3 \cdot HCl$) is a white to slightly yellow crystalline powder, and is very slightly soluble in water (0.2–0.5 mg/ml). There are several reported $pK_a$ values for amiodarone: 5.6 (Andreasen et al., 1981), 7.4 (Canada et al., 1981), and 6.56 (Bonati et al., 1984). Amiodarone carries a positive charge at pH values below its pKa. Amiodarone HCl has the following chemical structure:

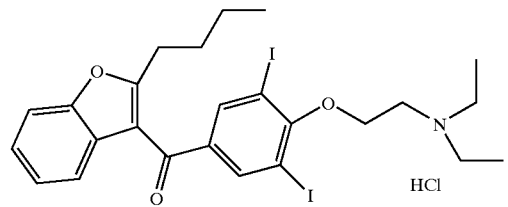

The solubility of amiodarone hydrochloride in water is reportedly highly temperature dependent. The solubility ranges from 0.3 to 0.5 mg/ml at 20° C. to about 7 mg/ml at 50° C. At about 60° C., the solubility increases to greater than 100 mg/ml. At concentrations of about 50 mg/ml, amiodarone reportedly forms colloidal structures about 100 nm in diameter and micelles containing approximately 150 monomeric units and having a molecular weight in excess of 100,000.

Due to its low intrinsic water solubility, amiodarone is difficult to formulate in a water-based parenteral formulation that is sufficiently concentrated and stable and present in a medium having a physiologically acceptable pH. The currently marketed formulation (CORDARONE® Intravenous; CORDARONE I.V.®) of amiodarone contains 50 mg/ml amiodarone HCl, 20.2 mg/mL benzyl alcohol and 100 mg/mL polysorbate 80 (TWEEN® 80; a nonionic surfactant, emulsifier, dispersant and/or stabilizer) in water. The CORDARONE I.V.® formulation is packaged in single use containers.

Polysorbate 80 and benzyl alcohol, however, are known to cause unwanted side effects. For example, polysorbate 80, either alone or in combination with benzyl alcohol, reportedly acts as a potent cardiac depressant and causes hypotension, cancer. Moreover, parenteral administration of benzyl alcohol has reportedly been associated with hemolysis, death and a number of other side effects.

Aside from unwanted side effects, additional problems are associated with parenteral administration of a drug in a surfactant-based vehicle. For example, when the drug is diluted in the bloodstream two physical changes occur: 1) the pH and tonicity of the formulation approaches that of the blood; and 2) the concentrations of surfactant and drug are decreased proportionally to each other. In both instances the original composition of the formulation is altered, and a physically unstable solution may result. Specifically, if the drug in this diluted composition is present at a concentration which is greater than its solubility, a supersaturated solution with the potential to precipitate is formed (Ward, G. H and S. H. Yalkowsky in *J. Parenter Sci. Technol.* Vol. 47; 4:161–5 (1993)).

A number of patents and scientific publications disclose parenteral preparations of amiodarone that reportedly have reduced side effects as compared to the currently marketed formulation. U.S. Pat. No. 5,234,949 to Ehrenpreis et al. discloses a parenteral solution of amiodarone (25–75 mg/ml) in a surfactant-free acetate buffer solution having a pH below 4 and more preferably within the range of 3.5–3.8. Ehrenpreis et al. disclose that the concentration and choice of the buffering agent are critical for physical stability in order to reduce precipitation or gel formation. Solutions containing amiodarone at concentrations of 15–50 mg/ml in an acetate buffer with a pH of between 3.2 and 3.8 cannot be diluted in glucose-saline water beyond 1 mg/ml without forming very opalescent or even milky solutions.

U.S. Pat. No. 6,143,778 to Gautier et al. discloses a parenteral formulation containing amiodarone, a buffer solution and a non-ionic hydrophilic surfactant. The hydrophilic surfactant is required in order avoid the above-mentioned problem associated with dilution of a buffered solution containing amiodarone hydrochloride. Solutions containing 1.5–8.0% wt. amiodarone were reportedly prepared in the presence of surfactant. Solutions containing 30–50 mg amiodarone/mL of solution at pH 2.4–3.8 were reportedly prepared in the presence of buffers such as acetate (0.1–0.3 M), phosphate (0.1–0.15 M), or glycine (0.2 M), where the ionic strength was maintained between 0.08–0.3 M. At higher ionic strengths, cloudy solutions were reported. Citrate reportedly was not suitable at any concentration. Suitable surfactants reportedly included nonionic hydrophilic compounds with HLB values in the range of 13–29, and present in concentrations of about 0.5–2.0%. Some stated examples were Pluronics®, Cremophors®, Tweens® and Solutols®. The formulation reportedly could be diluted to concentrations both approximating (~0.5–0.8 mg/mL) and below (0.1–0.15 mg/mL) the amiodarone micellar concentration.

Ravin et al. (*J. Pharm. Sci.* (1975), 64(11), 1830–1833) disclose that chloride ion suppresses the solubility of amiodarone and that sodium citrate and tartrate, in very low concentrations ranging from 0.002–0.008 M and at pH values of 4.3–5.4, increase the solubility of amiodarone to 4.8 and 6 mg/mL, respectively. At higher concentrations, however, the solubility was supressed. Under the conditions tested, acetate in any concentration decreased the solubility of amiodarone at pH 4–4.7. The ability to prepare more concentrated solutions of amiodarone was demonstrated to be temperature dependent. At 25° C., 40° C., and about 60° C., amiodarone concentrations of 0.35 mg/mL, 0.95 mg/mL and >13 mg/mL, respectively, could be achieved. The solution heated to 60° C. could be cooled to 25° C. without precipitation; however, it could not be diluted to below the critical micellar concentration without precipitation.

Ravin et al. (*J. Pharm. Sci.* (1969), 58(10), 1242–45) report that cetyldimethyl-benzylammonium chloride, sodium lauryl sulfate and tween 80 increased the solubility of amiodarone at surfactant concentrations up to 0.02% wt.

Cyclodextrins and their derivatives are widely used in liquid formulations to enhance the aqueous solubility of hydrophobic compounds. Cyclodextrins are cyclic carbohydrates derived from starch. The unmodified cyclodextrins differ by the number of glucopyranose units joined together in the cylindrical structure. The parent cyclodextrins contain 6, 7, or 8 glucopyranose units and are referred to as α-, β-, and γ-cyclodextrin respectively. Each cyclodextrin subunit has secondary hydroxyl groups at the 2 and 3-positions and a primary hydroxyl group at the 6-position. The cyclodextrins may be pictured as hollow truncated cones with hydrophilic exterior surfaces and hydrophobic interior cavities. In aqueous solutions, these hydrophobic cavities provide a haven for hydrophobic organic compounds, which can fit all, or part of their structure into these cavities. This process, known as inclusion complexation, may result in increased apparent aqueous solubility and stability for the complexed drug. The complex is stabilized by hydrophobic interactions and does not involve the formation of any covalent bonds.

Chemical modification of the parent cyclodextrins (usually at the hydroxyl moieties) has resulted in derivatives with sometimes improved safety while retaining or improving the complexation ability of the cyclodextrin. Of the numerous derivatized cyclodextrins prepared to date, only two appear to be commercially viable; the 2-hydroxypropyl derivatives (HP-β-CD or HPCD), neutral molecules being commercially developed by Jannsen and others, and the sulfoalkyl ether derivatives (SAE-β-CD or SAE-CD), being developed by CyDex, Inc.

The SAE-CDs are a class of negatively charged cyclodextrins, which vary in the nature of the alkyl spacer, the salt form, the degree of substitution and the starting parent cyclodextrin. The sodium salt of the sulfobutyl ether derivative of beta-cyclodextrin, with an average of about 7 substituents per cyclodextrin molecule (SBE7-β-CD), is being commercialized by CyDex, Inc. (Kansas) as CAPTISOL® cyclodextrin.

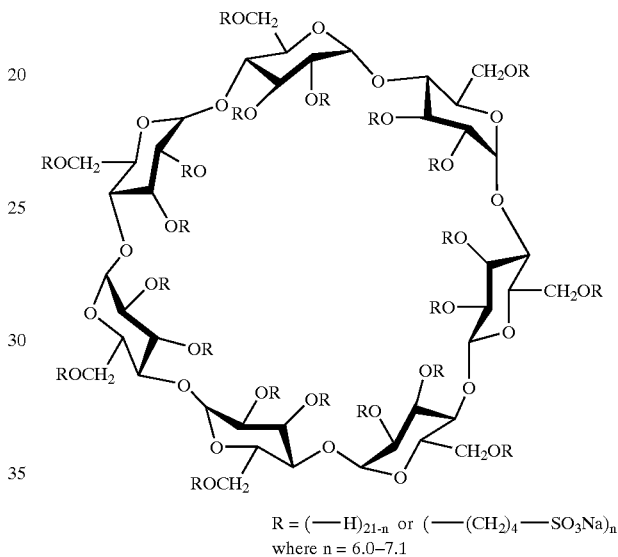

$R = (\text{---}H)_{21-n}$ or $(\text{---}(CH_2)_4\text{---}SO_3Na)_n$
where $n = 6.0–7.1$ Sulfobutyl Ether-β-Cyclodextrin (Captisol®)

The anionic sulfobutyl ether substituent dramatically improves the aqueous solubility of the parent cyclodextrin. Reversible, non-covalent, complexation of drugs with the CAPTISOL® cyclodextrin generally allows for increased solubility and stability of drugs in aqueous solutions.

It has been reported that the relative increase in the solubility of a poorly soluble drug in the presence of an SAE-CD is a product of the binding constant and the molar concentration of SAE-CD present (Stella et al. in U.S. Pat. Nos. 6,046,177 and 5,874,418). Compounds usually exhibit a conventional type $A_L$ ('A' Linear) binding curve (Higuchi, T. and Connors, K. A. in "Advances in Analytical Chemistry and Instrumentation Vol. 4" (Reilly, Charles N. Ed., John Wiley & Sons., 1965, pp. 117–212)) when binding to an SAE-CD. In a typical type $A_L$ profile, the total solubility of the drug (y-axis) in water increases linearly with increasing concentrations of cyclodextrin present (x-axis). The data usually fits a straight line and rarely deviates from this relationship unless the particular compound (drug) being solubilized possesses an unexpected binding relationship with the SAE-CD. The y-intercept of a best-fit line through the data is equal to the theoretical intrinsic solubility of the drug in water.

Equations 1 and 2 generally describe the dynamic and reversible binding equilibrium, where the amount of drug, for example, in the complexed form is a function of the concentrations of the drug and cyclodextrin, and the equilibrium or binding constant, $K_{1:1}$.

$$\text{Drug} + \text{Cyclodextrin} \xleftarrow{K_{1:1}} \text{Complex} \qquad \text{Equation 1}$$

$$K_{1:1} = \frac{[\text{Complex}]}{[\text{Drug}][\text{Cyclodextrin}]} \qquad \text{Equation 2}$$

CAPTISOL® cyclodextrin is relatively new and its combined use with amiodarone for parenteral administration has not been evaluated.

U.S. Pat. No. 6,267,985 to Chen et al. discloses a method for improving the solubilization of triglycerides and improved delivery of therapeutic agents. The disclosed formulations comprise a combination of two surfactants, a triglyceride and therapeutic agent that is capable of being solubilized in the triglyceride, the carrier, or both the triglyceride and the carrier. The '985 Patent suggests the use of amiodarone and of an optional solubilizing agent, such as a cyclodextrin, which can include cyclodextrin derivatives such as hydroxypropyl cyclodextrin (HPCD), sulfobutyl ether cyclodextrin and a conjugate of sulfobutyl ether cyclodextrin. HPCD is the preferred cyclodextrin.

U.S. Pat. No. 6,294,192 to Patel et al. discloses triglyceride-free oral pharmaceutical compositions capable of solubilizing therapeutically effective amounts of hydrophobic therapeutic agents. The disclosed formulations include a combination of a hydrophilic surfactant and a hydrophobic surfactant. The '192 Patent suggests the use of amiodarone and of an optional solubilizing agent, such as a cyclodextrin, which can include cyclodextrin derivatives such as HPCD and sulfobutyl ether cyclodextrin. HPCD is the preferred cyclodextrin.

U.S. patent application Ser. No. 20020012680 to Patel et al. discloses triglyceride-free pharmaceutical compositions comprising a hydrophobic therapeutic agent, and a carrier comprising at least one hydrophilic surfactant and at least one hydrophobic surfactant. The application claims but does not teach the use of amiodarone as a suitable hydrophobic therapeutic agent. The claimed formulation can further comprise a solubilizer, which may be a sulfobutyl ether cyclodextrin.

U.S. Pat. Nos. 5,874,418 and 6,046,177 to Stella et al. disclose sulfoalkyl ether cyclodextrin-containing solid pharmaceutical compositions and formulations, and methods for their preparation for the sustained, delayed or controlled delivery of therapeutic agents. The patents disclose formulations containing a physical mixture of a sulfoalkyl ether cyclodextrin and a therapeutic agent, and optionally at least one release rate modifier. Both patents teach that the relative increase in the solubility of a poorly soluble drug in the presence of sulfoalkyl ether cyclodextrins (SAE-CDs) is a product of the binding constant and the molar concentration of SAE-CD present. In other words, Stella et al. disclose that the binding of an SBE-CD to a drug is governed by the formula set forth above. Amiodarone is listed as one of a large number of drugs that can be used.

U.S. Pat. Nos. 5,134,127 and 5,376,645 to Stella et al. disclose parenteral formulations containing an SAE-CD and a drug. Amiodarone is not included in the list of drugs that can be used.

International Publication No. WO 91/13100 to Coates et al. discloses liquid formulations containing amiodarone and $6^A$-amino-$6^A$-deoxy-N-(3-carboxypropyl)-β-cyclodextrin (β-CDNSc) for IV injection. In an in vivo dog study, subjects were intravenously administered solutions containing 5 mg/kg amiodarone with or without β-CDNSc. AUC (0–24) and $C_{max}$ were increased following administration of the cyclodextrin-containing formulation, while no significant changes were found in the AUC (0–infinity) and elimination half-life. The β-CDNSc reportedly eliminated the common side effects observed after intravenous injection of amiodarone. The data regarding the half-life of amiodarone was highly variable (17.646 h+/−14.04 h (control) and 36.264 h+/−32.332 h).

International Publication No. 91/04026 to Palmer et al. discloses liquid formulations containing amiodarone with α-cyclodextrin, β-cyclodextrin, λ-cyclodextrin, δ-cyclodextrin, dimethyl-β-cyclodextrin, or aminocyclodextrin. An in vivo pig study was conducted wherein pigs were orally administered the amiodarone and aminocyclodextrin.

The safety of cyclodextrins is often compared by way of in-vitro hemolysis studies. As depicted in FIG. 1 (Thompson, D. O., Critical Reviews in Therapeutic Drug Carrier Systems, (1997), 14(1), 1–104), the hemolytic behavior of the CAPTISOL® cyclodextrin is compared to the same for the parent β-cyclodextrin, the commercially available hydroxypropyl derivatives, ENCAPSIN™ (degree of substitution~4; HP4-β-CD) and MOLECUSOL™ (degree of substitution~8; HP8-β-CD), and two other sulfobutyl ether derivatives, SBE1-β-CD and SBE4-β-CD. Unlike the other cyclodextrin derivatives, SAE-CD derivatives, in particular those such as the CAPTISOL® cyclodextrin (degree of substitution~7; SBE7-β-CD) and SBE4-β-CD (degree of substitution~4), show essentially no hemolytic behavior in concentrations typically used to solubilize pharmaceutical formulations. These SAE-CDs exhibit substantially lower membrane damaging potential than the commercially available hydroxypropyl derivatives.

Sulfated cyclodextrin derivatives have also been prepared and their effects on blood clotting time evaluated. Sulfated cyclodextrins were found to interfere significantly with blood clotting time, especially when compared to the sulfoalkyl ether cyclodextrins (Thompson, D. O., Critical Reviews in Therapeutic Drug Carrier Systems, (1997), 14(1), 1–104).

Methylated cyclodextrins have been prepared and their hemolytic effect on human erythrocytes has been evaluated. These cyclodextrins were found to cause moderate to severe hemolysis (Jodal et al., Proc. $4^{th}$ Int. Symp. Cyclodextrins, (1988), 421–425; Yoshida et al., Int. J. Pharm., (1988), 46(3), 217–222).

By virtue of their respective functional groups, derivatized cyclodextrins can differ in terms of their state of ionization when present in solutions at different pH values. The functional group of carboxy-β-cyclodextrins, (e.g. succinyl-β-cyclodextrin, $6^A$-amino-$6^A$-deoxy-N-(3-carboxypropyl)-β-cyclodextrin) typically has a pKa of approximately 3–5. Thus, carboxy cyclodextrins typically are charged in solutions at pH 3.5–14. As the pH decreases below the pKa of the functional groups of carboxy-β-cyclodextrin, the overall negative charge of the cyclodextrin decreases. The ionization state for neutral cyclodextrins such as HPCD does not change over the pharmaceutically relevant pH range. However, the sulfoalkyl ether cyclodextrin (SAE-CD), unlike most cyclodextrins, has a $pK_a$ of less than one, meaning that in solution, the SAE-CD remains fully ionized throughout the pH range usuable for drug formulation (pH 1–14). Although no literature is available regarding the change in ionization versus solution pH for the sulfate derivatized cyclodextrin, it is assumed that the sulfate derivatized cyclodextrins are also fully ionized over the pH range of 1–14.

The disclosures described above do not describe whether amiodarone is in an ionized state when administered or whether its carrier cyclodextrin is ionized upon administration.

Accordingly, of the different cyclodextrins mentioned above, only the sulfoalkyl ether cyclodextrins and the hydroxypropyl cyclodextrins have demonstrated sufficient safety to be suitable for parenteral administration.

None of the known art has been able to overcome the disadvantages inherent in the present CORDARONE® formulation and a need remains for improved parenteral formulations of amiodarone. A need remains for improved formulations that are readily dilutable from a concentrated solution while maintaining clarity, can be administered at a physiologically acceptable or relevant pH, remain chemically stable under a variety of storage conditions, are easier to handle and administer, and that reduce the severity or occurrence of the side effects, such as hypotension, bradycardia, hemolysis, and phlebitis, of presently marketed formulations of amiodarone. Additionally, an improved parenteral formulation that eliminates side effects associated with a surfactant or organic solvent is needed. None of the art discloses or suggests the invention as claimed herein.

SUMMARY OF THE INVENTION

The present invention seeks to overcome some or all of the disadvantages inherent in other known formulations. The invention provides a sulfoalkyl ether cyclodextrin (SAE-CD)-based parenteral formulation of amiodarone. The invention provides a commercially viable formulation that can be prepared and stored in aqueous liquids at a wide range of physiologically acceptable pH values and concentrations of amiodarone without significant precipitation of the amiodarone in vitro. The formulation is pharmaceutically stable with a wide range of buffers, saline, or lactated Ringers solutions. The formulation also has a greater surface tension than the presently marketed formulation and therefore allows for more accurate dosing when administered in drip counter infusion sets.

The SAE-CD and amiodarone-containing formulation has a sufficiently high amiodarone concentration and stability for use as a commercial product. The formulation can be prepared as a clear aqueous solution that is sterilizable by sterile filtration (for example, filter pore size of less than or equal to 0.22 µm) and other conventional methods. The liquid formulation is stable under a variety of storage conditions and can also be converted to a reconstitutable solid. The formulation can be administered by injection at a physiologically acceptable pH range. Depending upon the pH of the medium, the SAE-CD can be present in less than stoichiometric, stoichiometric, or greater than stoichiometric amounts with respect to the amount of amiodarone present and still provide a clear solution. For example, at low solution pH, i.e., pH that approximates or is below the pKa of amiodarone, and low concentrations of amiodarone and SAE-CD, less than stoichiometric amounts of SAE-CD can be used and can enhance the solubility of amiodarone predominantly by non-covalent ionic binding. At low and high solution pHs, i.e., pH greater than the pKa of amiodarone, and higher concentrations of amiodarone and SAE-CD, greater than stoichiometric amounts of SAE-CD can be used and can enhance the solubility of amiodarone by both non-covalent ionic binding and by complexation via the formation of inclusion complexes.

One aspect of the invention provides a clear liquid formulation comprising at least a therapeutically effective amount of an antiarrhythmic agent, such as amiodarone, and a sulfoalkyl ether cyclodextrin present in an amount sufficient to provide a clear solution and avoid precipitation when diluted with a pharmaceutically acceptable liquid excipient composition. The formulation can be provided as a stock solution, which is diluted with a liquid carrier composition such as saline, plasma, or lactated Ringer's solution prior to administration to a subject. Alternatively, the formulation can be provided at a concentration of amiodarone that is suitable for administration without dilution. Upon dilution with a pharmaceutically acceptable aqueous liquid carrier, the present formulations will not precipitate or will form less precipitate than a corresponding formulation not containing the SAE-CD. The present formulation does not require a surfactant in order to render the formulation suitable for dilution.

Specific embodiments of the invention include those wherein: 1) the liquid formulation is dilutable, the SAE-CD to amiodarone molar ratio is greater than or equal to about 1.1±0.01, the amiodarone concentration is in the range of less than or equal to about 3 mg/ml, the SAE-CD concentration is less than or equal to about 4.5 mM (0.9% wt.), and the pH of the liquid is less than or equal to about 5.8; 2) the liquid formulation is dilutable, the SAE-CD to amiodarone molar ratio is greater than or equal to about 1.1±0.01, the amiodarone concentration is greater than or equal to about 34 mg/mL (50 mM), the SAE-CD concentration is greater than or equal to about 55 mM, and the pH of the liquid medium approximates or is less than the pKa of amiodarone; 3) the formulation is provided as a reconstitutable buffered solid that provides a predetermined pH when dissolved in an unbuffered liquid carrier; 4) the SAE-CD is sulfobutyl ether 4-β-CD or sulfobutyl ether 7-β-CD; 5) the SAE-CD is a compound of the formula 1 (infra.) or a mixture thereof; 6) the liquid formulation further comprises a solubilizing agent, an antioxidant, a buffering agent, an acidifying agent, a complexation enhancing agent, saline, dextrose, a lyophilizing aid (for example, bulking agents or stabilizing agents), an electrolyte, another therapeutic agent, an alkalizing agent, an antimicrobial agent, an antifungal agent or a combination thereof; 7) the liquid formulation is lyophilized or otherwise dried to form a reconstitutable solid that provides a clear solution when reconstituted with an aqueous liquid; 8) the formulation comprises a buffering agent; 9) the formulation is dilutable to an amiodarone concentration of 1.5 mg/mL with a pharmaceutically acceptable aqueous liquid carrier without precipitation of amiodarone and without the addition of additional SAE-CD; 10) the liquid formulation comprises a higher concentration of amiodarone than another comparable formulation comprising another cyclodextrin derivative; and/or 11) the solution is a water dilutable concentrated stock solution having an amiodarone concentration greater than about 2.0 mg/mL.

Another aspect of the invention provides a clear ready-to-inject liquid formulation comprising SBE7-β-CD and amiodarone, wherein the SBE7-β-CD is present in an amount of at least about 0.3% wt., amiodarone is present in amount of 1–2 mg/mL.

Another aspect of the invention provides a dilutable concentrated liquid formulation comprising SBE7-β-CD and amiodarone is present in amount of greater than about 2 mg/mL and the SBE7-β-CD to amiodarone ratio is greater than or equal to about 1.1±0.01.

Another aspect of the invention provides a method of increasing the solubility of an acid-ionizable agent comprising the steps of:

providing an aqueous liquid comprising a sulfoalkyl ether cyclodextrin and an acid-ionizable agent, wherein the pH of the liquid approximates or is less than the pKa of the acid-ionizable agent, and the agent binds to the cyclodextrin predominantly by one or more non-covalent ionic bonds.

Specific embodiments of the invention include those wherein: 1) the acid-ionizable compound is amiodarone and the concentration of SAE-CD is less than about 0.025 M; 2) the aqueous liquid further comprises a salt or buffering agent present at a concentration of less than about 0.5 M; 3) the pH of the liquid is at least 0.1 pH units less than the pKa of the acid-ionizable agent; 4) the acid-ionizable agent comprises at least one acid-ionizable functional group selected from the group consisting of primary amine, secondary amine, tertiary amine, quaternary amine, aromatic amine, unsaturated amine, enol, primary thiol, secondary thiol, sulfonium, and hydroxyl; and/or 5) the pH of the liquid is no more than 0.5 pH units greater that the pKa of the acid-ionizable agent.

Other specific embodiments of the invention includes those wherein: 1) the formulation has been prepared at a temperature above 25° C., above 35° C., above 45° C. or above 50° C.; 2) the formulation has been prepared at a temperature approximating ambient temperature; and/or 3) the concentrated formulation is dilutable with a solution comprising SAE-CD and/or other solubilizing agent.

Still another aspect of the invention provides a reconstitutable solid pharmaceutical composition comprising an antiarrhythmic agent, an SAE-CD and optionally at least one other pharmaceutical excipient. When this composition is reconstituted with an aqueous liquid it forms a liquid formulation that can be administered by injection or infusion to a subject. Alternatively, the reconstitutable solid can form a concentrated reconstituted liquid.

The invention also provides a method of administering an antiarrhythmic agent comprising the step of administering a liquid formulation comprising a sulfoalkyl ether cyclodextrin and an antiarrhythmic drug. The formulation can be administered intravenously, subcutaneously, intradermally, intraperitoneally, or intramuscularly.

Specific embodiments of the methods of the invention include those wherein: 1) the liquid formulation is administered by injection or infusion; 2) the method further comprises the earlier step of mixing the SAE-CD and amiodarone, and optionally one or more ingredients, in a solution to form the liquid formulation; 3) the method further comprises the step of diluting the liquid formulation in a pharmaceutically acceptable liquid carrier prior to administration; 4) the method comprises the step of forming the liquid formulation by mixing a liquid carrier with a reconstitutable solid comprising the SAE-CD and amiodarone; 5) the liquid formulation is formulated as described herein; 6) the liquid formulation causes equivalent or less hypotension, bradycardia, and/or ventricular tachycardia in a subject as compared to presently marketed formulations; 7) the liquid formulation provides equivalent or improved chemical stability characteristics as compared to the presently marketed formulation of amiodarone; 8) the liquid formulation provides a heart-rate response similar to that of the marketed Cordarone® IV formulation; and/or 9) the liquid formulation provides a pharmacokinetic and/or pharmacodynamic profile similar to that of the marketed Cordarone® IV formulation.

The invention also provides methods of preparing an SAE-CD and antiarrthymic agent-based liquid formulation.

Another aspect of the invention provides a kit comprising a first pharmaceutical composition comprising an SAE-CD and a second pharmaceutical composition comprising an antiarrhythmic agent.

Other features, advantages and embodiments of the invention will become apparent to those skilled in the art by the following description, accompanying examples.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
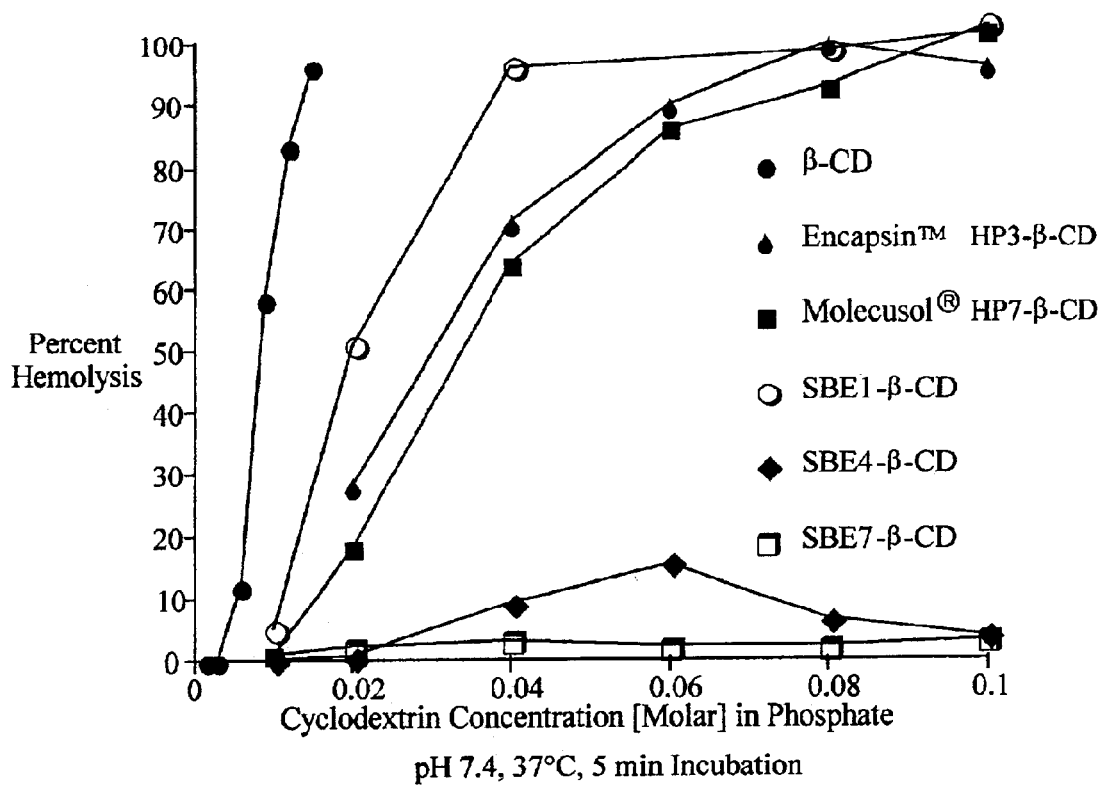
FIG. 1 depicts a prior art graph comparing the hemolytic activity of different cyclodextrins.

A formulation according to the invention comprising amiodarone and a sulfoalkyl ether cyclodextrin overcomes some or all known disadvantages present in prior art formulations of amiodarone. The present formulation generally excludes the harmful excipients found in the marketed amiodarone formulations. Moreover, the present formulation has an increased surface tension as compared to the CORDARONE® formulation. The present formulation is also dilutable at a broad range of pH values without formation of precipitate.

As used herein, the term amiodarone includes all neutral and salt forms of the same. N-desethylamiodarone (DEA) is the major active metabolite of amiodarone in humans. The term amiodarone also includes DEA and all of its neutral and salt forms.

As used herein the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

As used herein the term non-covalent ionic bond refers to a bond formed between an anionic species and a cationic species. The bond is non-covalent such that the two species together form a salt or ion pair. The SAE-CD provides the anionic species of the ion pair and the acid-ionizable agent provides the cationic species of the ion pair. Since the SAE-CD is multi-valent, an SAE-CD can form an ion pair with one or more acid-ionizable agents.

The degree to which an acid-ionizable agent is bound by non-covalent ionic binding versus inclusion complexation formation can be determined spectrophotometrically using methods such as $^1$HNMR, $^{13}$CNMR, or circular dichroism (CD), for example, and by analysis of the phase solubility data for the acid-ionizable agent and SAE-CD. The artisan of ordinary skill in the art will be able to use these conventional methods to approximate the amount of each type of binding that is occurring in solution to determine whether or not binding between the species is occurring predominantly by non-covalent ionic binding or inclusion complex formation. An acid-ionizable agent that binds to SAE-CD by both means will generally exhibit a bi-phasic phase solubility curve. Under conditions where non-covalent ionic bonding predominates over inclusion complex formation, the amount of inclusion complex formation, measured by NMR or CD, will be reduced even though the phase solubility data indicates significant binding between the species under those conditions; moreover, the intrinsic solubility of the acid-ionizable agent, as determined from the phase solubility data, will generally be higher than expected under those conditions.

As used herein the term reconstitutable solid is taken to mean a solid capable of dissolution in an aqueous liquid medium to form a reconstituted liquid, wherein after dissolution the liquid medium is visibly clear. A reconstitutable pharmaceutical formulation according to the present invention comprises an antiarrhythmic agent, an SAE-CD and optionally, at least one other pharmaceutical excipient. A reconstitutable solid can be prepared by removal of the liquid medium from an aqueous liquid solution comprising SAE-CD and amiodarone, and optionally other components to form the solid. The composition can comprise an admixture of a solid SAE-CD and an antiarrhythmic agent-containing solid comprising an antiarrhythmic agent and optionally at least one other solid pharmaceutical excipient, such that a major portion of the antiarrhythmic is not complexed with the SAE-CD prior to reconstitution. Alternatively, the composition can comprise a solid mixture of an SAE-CD and an antiarrhythmic agent, wherein a major portion of the antiarrhythmic agent is complexed with the SAE-CD prior to reconstitution. A reconstitutable solid will generally comprise less than 8% wt. water. The reconstitutable solid formulation provides equivalent or improved chemical stability of amiodarone as compared to the marketed Cordarone® formulation. This composition is reconstituted with an aqueous based solution to form a liquid formulation containing the antiarrhythmic agent and other agents that is administered by injection or infusion to a subject. The liquid formulation used in the preparation of a reconstitutable formulation may be prepared as described herein for the diluted or concentrated liquid formulations. It may also be prepared to contain an SAE-CD and the antiarrhythmic agent at concentrations greater than typically used in the liquid formulation of the invention, while maintaining the same SAE-CD to amiodarone agent molar ratio. A reconstitutable solid can be made to form a reconstituted liquid formulation that is or is not dilutable after the solid has been reconstituted with a predetermined amount of an aqueous liquid and at a predetermined temperature. A reconstituted liquid formulation that is not dilutable with water can be made by adding a sufficient amount of an aqueous liquid to a reconstitutable solid having an SAE-CD to amiodarone molar ratio of less than about 1.09 while heating. A reconstituted liquid formulation that is dilutable can be made by dissolving in water a reconstitutable solid comprising a mixture of SAE-CD and amiodarone having a molar ratio of greater than or equal to about 1.1±0.01. Applicants note that any composition according to the invention can be dissolved or diluted with another liquid containing SAE-CD.

The reconstitutable composition is prepared according to any of the following processes. A liquid formulation of the invention is first prepared, then a solid is formed by lyophilization (freeze-drying), spray drying, spray freeze-drying, vacuum-drying, antisolvent precipitation, various processes utilizing supercritical or near supercritical fluids, or other methods known to those of ordinary skill in the art to make a powder or a solid suitable for reconstitution.

A reconstitutable solid can be a powder, glassy solid, porous solid, or particulate. The reconstitutable solid can be crystalline or amorphous.

As used in regards to an SAE-CD-containing composition or formulation according to the invention, the term dilutable refers to a liquid formulation containing SAE-CD and an active agent, such as amiodarone for example, wherein the formulation can be further diluted (with water or dextrose (5%) in water at room temperature, e.g., ambient temperature such as a temperature of about 20°–28° C.) without precipitation, i.e. if precipitation occurs it is less than or equal to about 3% wt. (in other words, precipitation is insignificant), of the active agent while maintaining a clear solution when diluted to an amiodarone concentration of about 1.5 mg/mL. A dilutable SAE-CD and active agent-containing liquid can be diluted with another solution that does not contain SAE-CD and the resulting diluted solution will have a lower concentration of active agent without affecting significant precipitation of the active agent. Accordingly, an SAE-CD and active agent-containing solution that is not dilutable according to the invention will form a significant amount (>3% wt. of active agent) of precipitate when diluted with another solution.

It should be noted that a solution that is not dilutable with water at room temperature may be rendered dilutable with a solution that contains SAE-CD as long as the final molar ratio of amiodarone to SAE-CD in the diluted solution is within the required range as described herein. Example 15 details a procedure wherein 23 microliters of a solution (pH 3.5 at 25° C. with ~25 mM citrate buffer containing SAE-CD (23% w/v) and amiodarone hydrochloride (68.2 mg/mL) and having an SAE-CD to amiodarone molar ratio of 1.02 is diluted with 977 microliters of another solution (dextrose 5% in water at 25° C.) containing SAE-CD (0.037 mM). The diluted solution has an SAE-CD to amiodarone ratio of 1.19 and is clear. The invention therefor provides a method of rendering dilutable a previously non-dilutable (as defined herein) amiodarone-containing solution comprising the step of diluting the previously non-dilutable solution with a second solution containing SAE-CD such that the molar ratio of SAE-CD to amiodarone in the diluted solution is $\geq 1.1 \pm 0.01$.

Temperature will have an effect upon the dilutability of a solution. In general, the determination of whether or not a solution is dilutable is made at approximately 25° C. or ambient temperature, e.g., 20°–28° C. A solution that is not dilutable at about 25° C. can be made dilutable with water at room temperature by dilution at an elevated temperature, such as >30° C., >40° C., >50° C. or higher. This heated dilution can be performed by diluting the first 25° C. solution with a heated solution or by mixing and heating two solutions which are initially at ambient temperature. Alternatively, the two solutions can be heated separately and then mixed.

Dilutability of an SAE-CD and amiodarone-containing solution at ambient temperature is particularly important in the clinical setting wherein solutions are not typically heated prior to mixing. Accordingly, the present invention provides solutions of amiodarone that can be diluted at ambient temperature without the need of a surfactant, organic solvent, soap, detergent or other such compound.

As used herein, a pharmaceutically acceptable liquid carrier is any aqueous medium used in the pharmaceutical sciences for dilution or dissolution of parenteral formulations.

The formulation of the invention comprises amiodarone and a sulfoalkyl ether cyclodextrin of the formula 1:

Formula 1

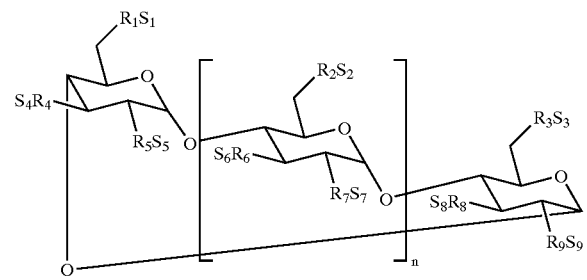

wherein:

n is 4, 5 or 6;

$R_1$, $R_2$, $R_3$, $R_4$, $R_5$, $R_6$, $R_7$, $R_8$ and $R_9$ are each, independently, —O— or a —O—($C_2$–$C_6$ alkylene)-$SO_3^-$ group, wherein at least one of $R_1$ and $R_2$ is independently a —O—($C_2$–$C_6$ alkylene)-$SO_3^-$ group, preferably a —O—$(CH_2)_m SO_3^-$ group, wherein m is 2 to 6, preferably 2 to 4, (e.g. —$OCH_2CH_2CH_2SO_3^-$ or —$OCH_2CH_2CH_2CH_2SO_3^-$); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$–$C_6$)-alkylamines, piperidine, pyrazine, ($C_1$–$C_6$)-alkanolamine and ($C_4$–$C_8$)-cycloalkanolamine.

The SAE-CD used in the liquid or solid formulation is described in U.S. Pat. Nos. 5,376,645 and 5,134,127 to Stella et al, the entire disclosures of which are hereby incorporated by reference. The preparation process may comprise dissolving the cyclodextrin in aqueous base at an appropriate temperature, e.g., 70° to 80° C., at the highest concentration possible. For example, to prepare the cyclodextrin derivatives herein, an amount of an appropriate alkyl sultone, corresponding to the number of moles of primary CD hydroxyl group present, is added with vigorous stirring to ensure maximal contact of the heterogeneous phase. According to one embodiment, the SAE-CD is SBE-7-β-CD (CAPTISOL® cyclodextrin), or SBE-4-β-CD.

The terms "alkylene" and "alkyl," as used herein (e.g., in the -0-($C_2$–$C_6$-alkylene)$SO_3^-$ group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The present invention provides compositions containing a mixture of cyclodextrin derivatives, having the structure set out in formula (I), where the composition overall contains on the average at least 1 and up to 3n+6 alkylsulfonic acid moieties per cyclodextrin molecule. The present invention also provides compositions containing a single type of cyclodextrin derivative, or at least 50% of a single type of cyclodextrin derivative.

The cyclodextrin derivatives of the present invention are obtained as purified compositions, i.e., compositions containing at least 90 wt. % or 95 wt. % of cyclodextrin derivative(s). In a preferred embodiment, purified compositions containing at least 98 wt. % cyclodextrin derivative(s) are obtained.

In some of the compositions of the invention unreacted cyclodextrin has been substantially removed, with the remaining impurities (i.e., <5 wt. % of composition) being inconsequential to the performance of the cyclodextrin derivative-containing composition.

Exemplary SAE-CD derivatives include SBE4-β-CD, SBE7-β-CD, SBE11-β-CD, and SBE4-γ-CD which correspond to SAE-CD derivatives of the formula I wherein n=5, 5, 5 and 6; m is 4; and there are 4, 7, 11 and 4 sulfoalkyl ether substituents present, respectively. It has been found that these SAE-CD derivatives increase the solubility of poorly water soluble drugs, such as amiodarone, to varying degrees in ways that have not been suggested or disclosed by the prior art.

By "therapeutic agent/SAE-CD complex" is generally meant a clathrate or inclusion complex of a sulfoalkyl ether cyclodextrin derivative of the formula (1) and a therapeutic agent. The ratio of therapeutic agent:SAE-CD present in the molecular complex can vary and can be in the range of about 0.33 to about 3, on a molar basis. In another embodiment of the dosage forms described herein, the ratio of therapeutic agent:SAE-CD is in the range of about 0.05 to about 20 on a molar basis, about 0.1 to about 10 or about 0.25 to about 2.5 on a molar basis. Thus, the SAE-CD will generally be, but need not be, present in excess of the therapeutic agent. The amount of excess will be determined by the intrinsic solubility of the agent, the expected dose of the agent, and the binding constant for inclusion complexation between the specific drug (agent) and the specific SAE-CD.

By "complexed" is meant "being part of a clathrate or inclusion complex with", i.e., a complexed therapeutic agent is part of a clathrate or inclusion complex with a sulfoalkyl ether cyclodextrin derivative. By "major portion" is meant at least about 50% by weight of the therapeutic compound. In various specific embodiments, greater than 50%, 60%, 75%, 90% or 95% by weight of the therapeutic agent can be complexed with an SAE-CD while in the pharmaceutical formulation. The actual percent of drug that is complexed will vary according to the complexation equilibrium constant characterizing the complexation of a specific SAE-CD to a specific drug and to the concentrations of SAE-CD and drug available for complexation.

Under conditions wherein the SAE-CD can form one or more ionic bonds with a positively charged acid-ionizable compound, the SAE-CD can be present in low concentrations and the ratio of drug to SAE-CD can be greater than one. Therefore, it is possible for less than 50% of the drug to be complexed, by way of an inclusion complex, with the SAE-CD and more or less than 50% of the drug to be non-covalently ionically bound to the SAE-CD.

SAE-CD solubilizes amiodarone significantly better than any other derivatized cyclodextrin regardless of whether the other derivatized cyclodextrin is negatively charged or neutral. The table below includes a comparison of the solubilization of amiodarone by several different cyclodextrins: 1) succinyl derivative having a degree of substitution of about 3, contains a functional group spaced 3 carbons from the cyclodextrin cavity capable of becoming negatively charged as pH values approach and move above the pKa (pKa ~4–5, Cyclolab, Budapest, Hungary); 2) sulfate derivative having a degree of substitution of about 14, contains a sulfate functional group located close to the cyclodextrin cavity that is fully ionized at pH 1–14, (Sigma-Aldrich, St. Louis, Mo., USA); 3) methyl derivative having a degree of substitution of about 14 no charge over the pH range 1–14, dimethyl-beta cyclodextrin, (Sigma-Aldrich, St. Louis, Mo., USA); 4) 2-hydroxypropyl derivative (HP8-β-CD) having a degree of substitution of about 8, neutral over the pH range 1–14, (Research Diagnostics, Inc, Flanders, N.J., USA); 5) 2-hydroxypropyl derivative (HP4-β-CD) having a degree of substitution of about 4, neutral over the pH range 1–14, (Research Diagnostics, Inc, Flanders, N.J., USA); and 6) sulfobutyl ether derivative, according to the invention, having a degree of substitution of about 7.

As shown in the table, SBE7-β-CD is 39 times, 138 times, 1.7 times, 3.3 times, and 3.6 times more effective at solubilizing amiodarone than the succinyl derivative, sulfate derivative, methyl derivative, HP8-β-CD, and HP4-β-CD, respectively at room temperature, pH 4.5 and 0.09 M cyclodextrin. Similar observation can be made at pH 7 and at other cyclodextrin concentrations.

| β-Cyclodextrin derivative | Cyclodextrin Concentration (M) | Amiodarone HCl Solubility (mg/ml) | | |
|---|---|---|---|---|
| | | pH 4.5 | pH 7.0 | pH 8.0 |
| Succinyl (DS~3) | 0.09 | 1.10 | 0.28 | |
| | 0.13 | 3.47 | 0.46 | |
| Sulfate (DS~14) | 0.09 | 0.31 | 0.09 | |
| | 0.13 | 0.70 | 0.11 | |
| Methyl (DS~14) | 0.09 | 24.54 | 6.32 | |
| | 0.13 | 24.93 | 9.54 | |
| 2-hydroxypropyl (DS~8) | 0.09 | 12.83 | 0.10 | 0.04 |
| | 0.13 | 15.75 | 0.29 | 0.17 |
| 2-hydroxypropyl (DS~4) | 0.09 | 11.76 | 0.09 | 0.03 |
| | 0.13 | 14.87 | 0.25 | |
| sulfobutyl ether (DS~7) | 0.09 (~20 wt. %) | 42.73 | 7.20 | 1.06 |
| | 0.13 (~30 wt. %) | 51.07 | 9.92 | 1.50 |

The data above indicate that the SAE-CD provides improved solubility of amiodarone relative to the other cyclodextrins regardless of the pH of the medium, or the charge state of the comparator cyclodextrin. Accordingly, the present invention provides an improved method of solubilizing amiodarone comprising the step of including an SAE-CD in a parenteral formulation comprising amiodarone.

Phase solubility data indicate that when amiodarone is complexed with sulfobutyl ether-7-β-cyclodextrin (SBE7-β-CD), it does not follow a typical type $A_L$ binding curve. In other words, the solubility of amiodarone when complexed with SBE7-β-CD is markedly higher than would be expected at pH 4.5. The binding curve for amiodarone with SBE7-β-CD at cyclodextrin concentrations of 10 to 40% w/v extrapolates to an unexpectedly high value for the y-intercept, implying a water solubility of amiodarone many times greater than its reported value of 0.2–0.5 mg/ml (0.00029–0.00073 Molar). Further evaluation of the binding isotherm at SBE7-β-CD concentrations from zero to about 0.025M shows an unexpected dramatic increase in amiodarone solubility with modest increase in the SBE7-β-CD concentration. At pH 4.5, a solution of 0.023 M SBE7-β-CD is able to solubilize up to about 0.04 M (27 mg/ml) of amiodarone. However, the HP4-β-CD or HP8-β-CD, at the same molar concentrations, are only able to solubilize about 0.007 moles (5 mg/ml) of amiodarone at pH 4.5.

Figure 2:
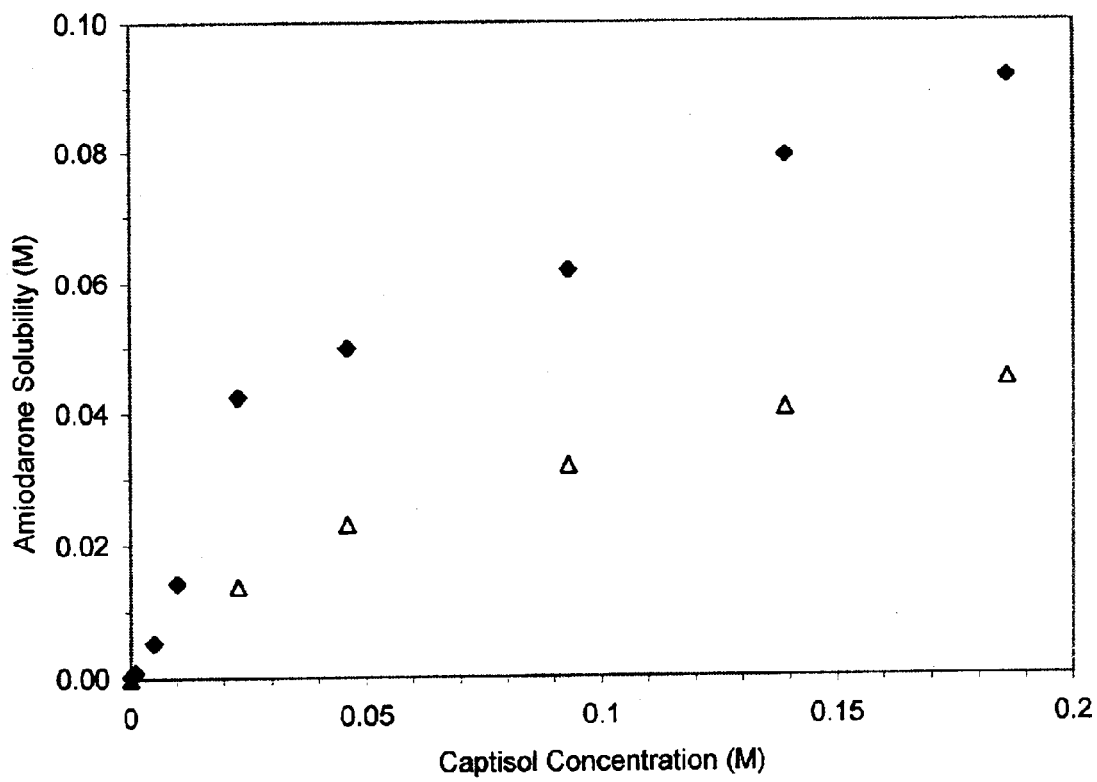
FIG. 2 depicts the data obtained from a room temperature phase solubility study conducted with amiodarone hydrochloride and SBE7-β-CD in water adjusted to pH 4.5 (♦), in 0.5M citrate buffer at pH 4.5 (Δ).

FIG. 2 depicts a phase solubility curve for SBE7-β-CD and amiodarone at pH 4.5 (pH adjusted with hydrochloric acid/sodium hydroxide) and at about 25° C. The data indicate the presence of two-phases of binding, wherein one type of binding dominates at low amiodarone and low cyclodextrin concentration and another type of binding dominates at higher amiodarone and higher cyclodextrin concentration. At pH values where the amiodarone is partially or fully ionized, (~pH<6)ionic binding between amiodarone and the cyclodextrin dominates when the SAE-CD concentration approximates or is below about 0.025 M and the amiodarone concentration approximates or is below about 0.045 M. Over the same pH range, inclusion complex formation between amiodarone and the cyclodextrin dominates when the SAE-CD concentration is above about 0.025 M and the amiodarone concentration approximates or is above about 0.045 M. This unique biphasic binding property has not been observed with other cyclodextrins and acid-ionizable agents. FIG. 2 also depicts a phase solubility curve for the solubility of amiodarone in the presence of 0.5M citrate buffer, pH 4.5 and increasing amounts of SBE7-β-CD. The presence of the charges present on the buffer eliminate most if not all of the non-covalent binding that results in increased solubility of amiodarone as described above. Thus the bi-phasic binding characteristic of an SAE-CD with amiodarone can changed to conventional linear binding, wherein binding occurs predominantly via inclusion complex formation, by the addition of charged species. Accordingly, the invention provides a method of improving the solubility of an acid-ionizable agent comprising the step of mixing the acid-ionizable agent with a negatively charged cyclodextrin to form a mixture having a pH less than or approximating the pKa of the acid-ionizable agent. The mixture can optionally further comprise a buffer or other charged species wherein the concentration of the buffer or other charged species is less than about 0.5M.

Figure 3:
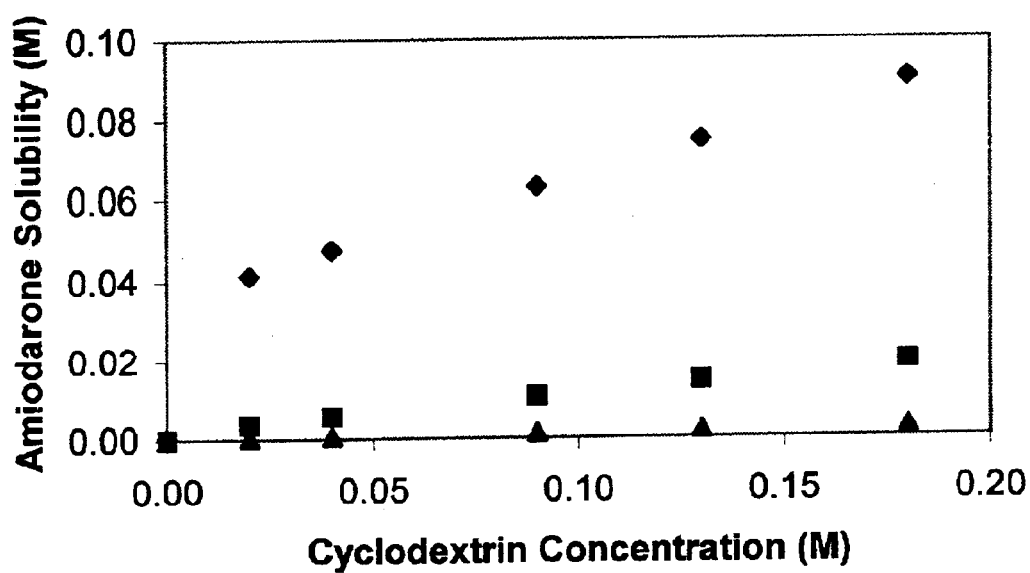
FIG. 3 depicts the data obtained from a room temperature phase solubility study conducted with amiodarone hydrochloride and SBE7-β-CD in water adjusted to pH 4.5 (♦), 7.0 (■), and 8.0 (▲).

FIG. 3 depicts the results of a phase solubility study conducted with amiodarone hydrochloride and SBE7-β-CD in water adjusted to pH 4.5 (♦), 7.0 (■), and 8.0 (▲). At pH values above the pKa of amiodarone, the amiodarone is predominately uncharged; therefore, binding with an SAE-CD occurs predominantly through inclusion complexation and the overall solubilization capability is reduced as compared to the solubilization observed at pH 4.5.

Figure 4:
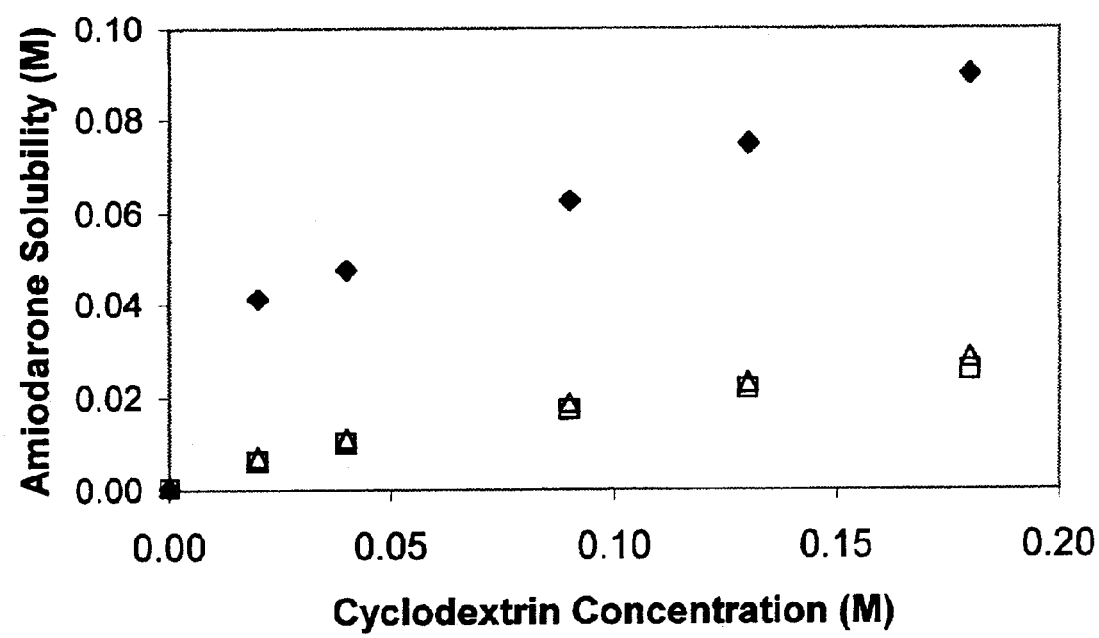
FIG. 4 depicts the data obtained from a room temperature phase solubility study conducted with amiodarone hydrochloride and the cyclodextrins SBE7-β-CD (♦), HP4-β-CD (□) and HP8-β-CD (Δ) in water adjusted to pH 4.5.

Even though the prior art suggests that HPCD is a preferred cyclodextrin for the solubilization of amiodarone, an SAE-CD has now been found to provide even better solubilization of amiodarone at all pH values tested. FIG. 4 depicts the data obtained from a phase solubility study conducted with amiodarone hydrochloride and the cyclodextrins SBE7-β-CD (♦), HP4-β-CD (□) and HP8-β-CD (Δ) in water adjusted to pH 4.5. Unlike the SBE7-β-CD, the HPCD's do not exhibit ionic binding with the amiodarone and are also poorer solubilizers of amiodarone.

Figure 5:
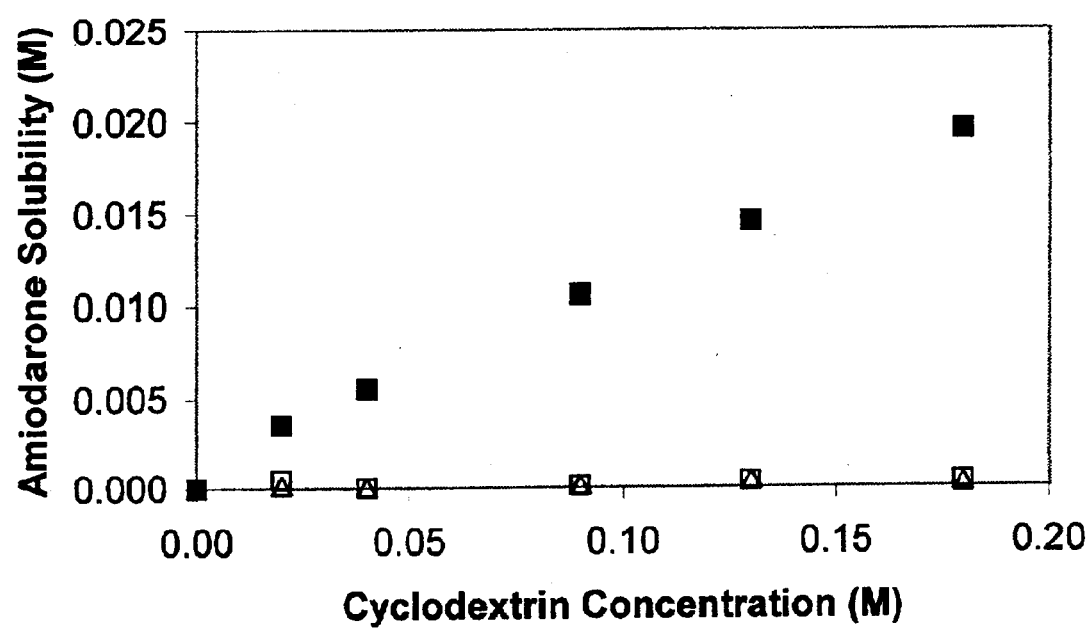
FIG. 5 depicts the data obtained from a room temperature phase solubility study conducted with amiodarone hydrochloride and the cyclodextrins SBE7-β-CD (■), HP4-β-CD (□) and HP8-β-CD (Δ) in water adjusted to pH 7.0.
Figure 6:
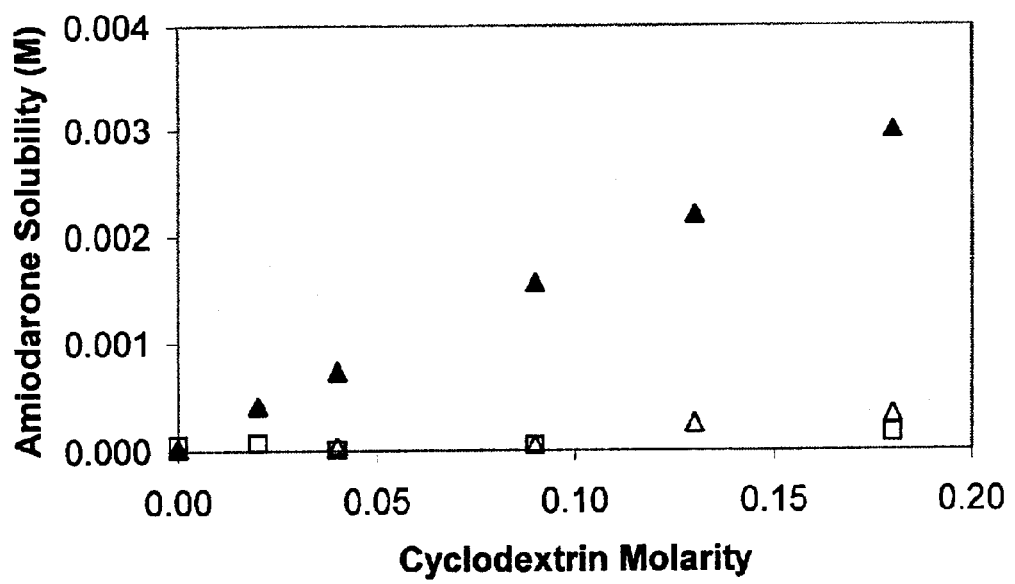
FIG. 6 depicts the data obtained from a room temperature phase solubility study conducted with amiodarone hydrochloride and the cyclodextrins SBE7-β-CD (▲), HP4-β-CD (□) and HP8-β-CD (Δ) in water adjusted to pH 8.0.

Unlike other cyclodextrins, an SAE-CD can solubilize amiodarone even at elevated pHs. FIG. 5 depicts the data obtained from a phase solubility study conducted with amiodarone hydrochloride and the cyclodextrins SBE7-β-CD (■), HP4-β-CD (□) and HP8-β-CD (Δ) in water adjusted to pH 7.0. FIG. 6 depicts the data obtained from a phase solubility study conducted with amiodarone hydrochloride and the cyclodextrins SBE7-β-CD (▲), HP4-β-CD (□) and HP8-β-CD (Δ) in water adjusted to pH 8.0. The HPCD's did not effectively solubilize amiodarone at either pH.

The temperature at which the SAE-CD and amiodarone are mixed influences the achievable maximum concentration of amiodarone in solution. Without heating, amiodarone concentrations as high as at least 100 mg/mL can be achieved in the presence of SAE-CD (0.37 M; 80% wt.) resulting in an SAE-CD to amiodarone molar ratio of about 2.5. However, if mixing of the components is performed at 50° C. or higher, then clear solutions having even higher amiodarone concentration can be prepared even though the molar ratio of SAE-CD to amiodarone is less than 1.09. The table below details the result obtained from studies on the effect of temperature upon the binding of amiodarone by SBE7-β-CD. It should be noted that each of the solutions below was clear after cooling to room temperature. In addition, the maximum achievable concentration for amiodarone was not reached at least for the procedure conducted with 50% wt. SAE-CD, i.e., the concentration of amiodarone listed is less than the maximum determined by clarity.

| SBE7-β-CD | | Amiodarone | | Ratio | |
|---|---|---|---|---|---|
| % w/v | Molar | Molar | mg/mL | ami:sbe | sbe:ami |
| 15 | 0.069 | 0.213 | 145 | 3.074 | *0.326 |
| 30 | 0.139 | 0.392 | 267 | 2.826 | *0.354 |
| 50 | 0.231 | 0.323 | 220 | 1.397 | *0.716 |

*denotes not dilutable with D5W (dextrose 5% in water) at room temperature without the formation of precipitate.

An amiodarone concentration of at least 260 mg/mL was achieved even though the molar ratio of SBE7-β-CD to amiodarone was less than 1.09. It should be noted that amiodarone concentrations greater than 267 mg/mL are achievable with the liquid formulation of the invention. While the two formulations detailed in the above table are not dilutable with water alone, they are dilutable with water containing SAE-CD provided that the final SAE-CD to amiodarone molar ratio is ≧ about 1.1±0.01. When the dilution is conducted at elevated temperature, e.g., ≧50° C., the concentrated solution can be diluted to form a diluted solution having an SAE-CD to amiodarone molar ratio of less than about 1.1. In the embodiments above, the molar ratio of amiodarone to SAE-CD is greater than or equal to about 0.3 and the liquid formulation has been exposed to a temperature of greater than or equal to about 45° C.

It should be noted that there is a significant difference between maximum achievable concentrations of amiodarone and whether or not a particular solution is dilutable with water alone. An SAE-CD can be used to solubilize amiodarone to obtain very high concentrations even though the SAE-CD to amiodarone molar ratio is less than 1.1. These high concentrations can be achieved regardless of whether or not the solution has been heated during mixing. Without heating, amiodarone concentrations of about 35 mg/ml can easily be achieved even in formulations having an SAE-CD to amiodarone molar ratio less than 1.1. With heating, even higher concentrations of amiodarone can be achieved as described herein. In other words, regardless of whether or not the aqueous medium, SAE-CD and amiodarone mixture is heated during mixing, it has been discovered that a dilutable liquid formulation is best achieved when the SAE-CD to amiodarone molar ratio is greater than or equal to about 1.1±0.01. Liquid formulations having an SAE-CD to amiodarone molar ratio of less than or equal to about 1.09±0.01 are generally not dilutable with distilled water or other liquid not containing a surfactant, soap, detergent, solubilizing agent, solvent, or cyclodextrin. If it is desired to dilute a solution having an SAE-CD to amiodarone concentration of <1.1, dilution can be accomplished by including SAE-CD and/or another conventional solubilizing agent (surfactant, soap, detergent, solvent, and others known to those of ordinary skill in the art) in the diluent solution.

In view of the temperature dependence of the dissolution of amiodarone by SAE-CD, the maximum amount of amiodarone that can be solubilized without heating is generally lower than can be solubilized with heating. By extrapolation of data obtained from phase solubility studies conducted at about 25° C., without heating, amiodarone concentrations of up to about 100 mg/mL can be achieved in the presence of SAE-CD.

The following table can be used to predict the ratio of components required to achieve the indicated amiodarone concentrations at room temperature (not heated) and pH 4.5. Each of the solutions described below is visibly clear; however, not all of the solutions are dilutable.

| SBE7-β-CD | | Amiodarone (Ami) | | Ratio | |
|---|---|---|---|---|---|
| % w/v | Molar | Molar | mg/mL | ami:sbe | sbe:ami |
| 0.5 | 0.00231 | 0.000708 | 0.482 | 0.306 | 3.265 |
| 1 | 0.00462 | 0.0045 | 3.0 | 0.973 | *1.027 |
| 3 | 0.0139 | 0.03019 | 20.6 | 2.177 | *0.459 |
| 5 | 0.0231 | 0.0423 | 28.8 | 1.830 | *0.546 |
| 30 | 0.139 | 0.079 | 53.8 | 0.570 | 1.756 |

-continued

| SBE7-β-CD | | Amiodarone (Ami) | | Ratio | |
|---|---|---|---|---|---|
| % w/v | Molar | Molar | mg/mL | ami:sbe | sbe:ami |
| 50 | 0.231 | 0.106 | 72.2 | 0.459 | 2.181 |
| 80 | 0.370 | 0.148 | 100.8 | 0.400 | 2.499 |

*denotes solutions that are not dilutable with D5W at room temperature without the formation of precipitate.

For an amiodarone concentration of about 1.5 mg/mL, the SAE-CD concentration is about 0.3% w/v in one exemplary embodiment.

Were a solution containing amiodarone and SAE-CD to follow the type typical $A_L$ linear binding profile, one would expect that the ratio of amiodarone to SAE-CD would be essentially constant for the entire concentration range and all resulting solutions would be dilutable. However, it has been discovered that amiodarone and SBE7-β-CD behave atypically in acidic solutions at room temperature when the concentrations of amiodarone and cyclodextrin are low.

Figure 9:
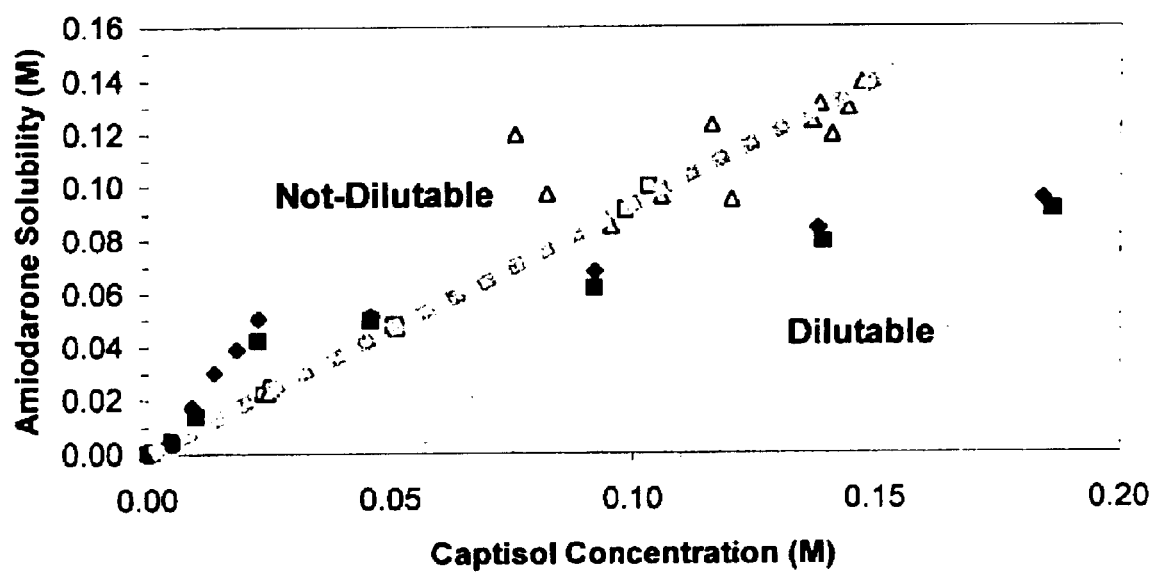
FIG. 9 depicts compositions for various solutions containing amiodarone HCl and SBE7-β-CD. The solid symbols represent solutions prepared at room temperature and the open symbols represent solutions prepared at temperatures >50° C. then cooled. The line indicates an approximate division between solutions that are dilutable and solutions that are not dilutable.

At higher concentrations of SAE-CD where the concentration of SAE-CD in solution increases from 15%, the maximum achievable concentration of amiodarone in solution increases and the ratio of SBE7-β-CD to amiodarone required to achieve that concentration increases. At lower concentrations of SAE-CD where the concentration of SAE-CD is below about 0.5%, the maximum achievable concentration of amiodarone in solution increases with increasing SBE7-β-CD concentration, and the ratio of SBE7-β-CD to amiodarone required to achieve that concentration increases. However, in the SAE-CD concentration of range of about 0.5% to 12%, the molar ratio of SBE7-β-CD to amiodarone at maximal achievable amiodarone concentrations, is less than about 1.1% resulting in solutions that are not dilutable according to the invention; although, the solutions are clear when formed. FIG. 9, discussed below, further details this unexpected phenomenon.

A single-phase binding curve can also be achieved by selecting the appropriate buffering agent. A formulation according to the present invention can include a wider range of buffers than other known amiodarone-containing liquid formulations. Suitable buffering agents include citrate, acetate, phosphate, tris, borate and others. As noted above, the ionic strength of the buffer in solution can affect the occurrence of biphasic phase solubility curve. If the bi-phasic nature is desired, the ionic strength of the buffer will generally be less than about 0.5 M depending upon the identity of the buffer. It should be noted that the total ionic strength of charged species in solution, excluding amiodarone and SAE-CD, is preferably less than about 0.5 M.

Figure 7:
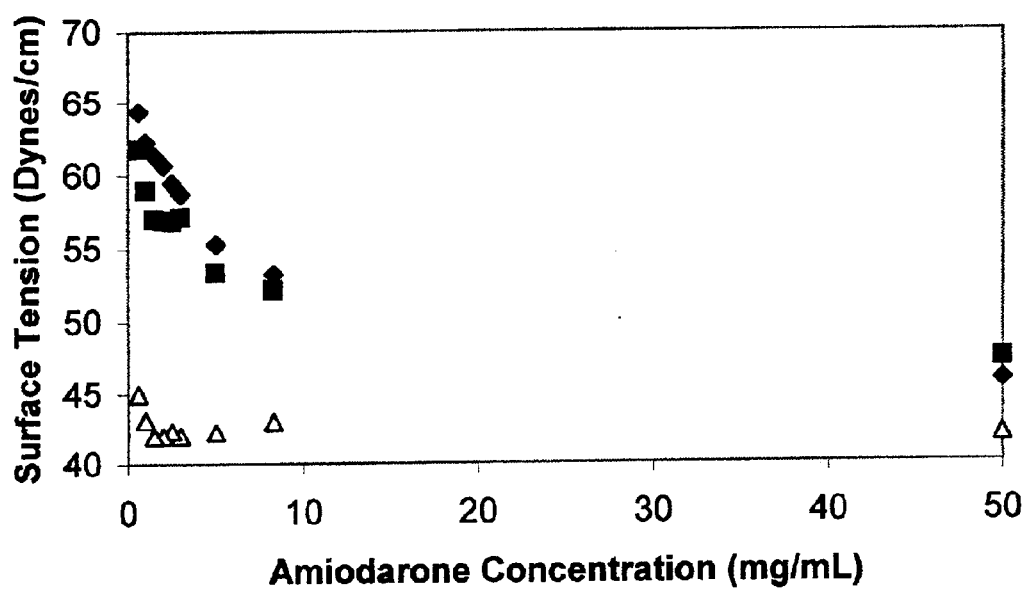
FIG. 7 depicts the data obtained from a room temperature surface tension study conducted with SBE7-β-CD (pH 4.5 (♦) and pH 6.0 (■)) and the amiodarone HCl marketed formulation (Δ) at pH 3.9. Dextrose 5% in water was used for dilutions of the stock formulations.

One of the difficulties of administering the commercially available CORDARONE® formulation by drip infusion bag is its low surface tension. It is generally desirable to have a liquid formulation with a surface tension approximating that of water (~72 dynes/cm) so that uniform drop-size, and thereby more accurate drug administration, can be achieved. FIG. 7 depicts the data obtained from a surface tension study conducted with SBE7-β-CD (30% wt; pH 4.5 (◆) and pH 6.0 (■)) and the marketed amiodarone HCl formulation (Δ) at pH 3.9. In this example, all three formulations were diluted with D5W. At high amiodarone concentrations that are suitable for use as stock solutions for dilution into i.v. infusion bags or bottles, the surface tension of the SAE-CD containing formulation is higher than but still close to that of the marketed amiodarone HCl formulation. At low amiodarone concentrations (≦10 mg/mL or approximating those at which amiodarone is administered in the clinic, e.g., 1.5 mg/mL), the SAE-CD containing formulation can be made to have a much higher surface tension (greater than about 50 dynes/cm) and is more suitable for administration by i.v. drip infusion. Accordingly, the invention provides an improved amiodarone containing parenteral formulation comprising an SAE-CD and amiodarone having a surface tension higher than that of the CORDARONE® formulation.

Figure 8:
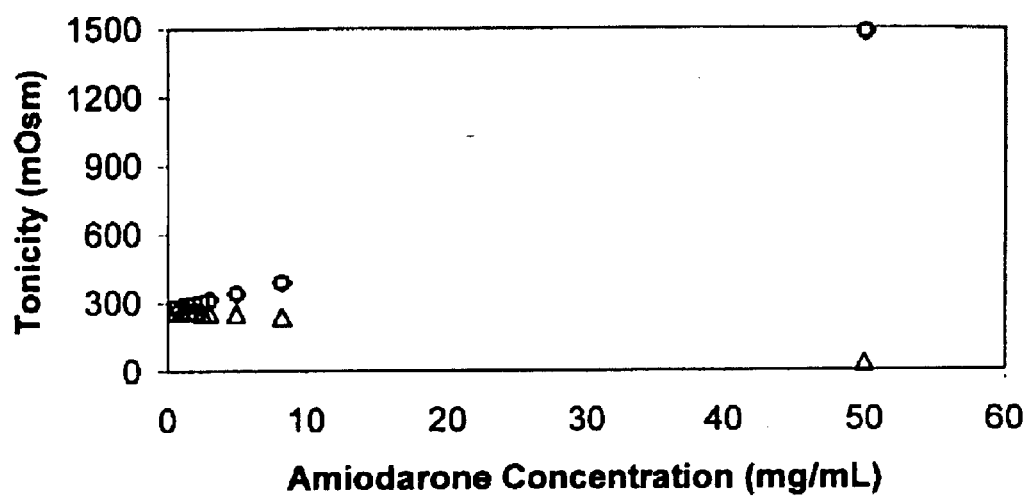
FIG. 8 depicts the data obtained from a room temperature tonicity study conducted with SBE7-β-CD (pH 4.5 (♦) and pH 6.0 (□)) and the amiodarone HCl marketed formulation (Δ) at pH 3.9. Dextrose 5% in water was used for dilutions of the stock formulations.

Tonicity is another important aspect of a parenteral formulation. The present formulation provides a parenteral formulation that is approximately isotonic in the ready-to-inject or diluted form and hypertonic in the concentrated form. FIG. 8 depicts data obtained from a tonicity study conducted with SBE7-β-CD (30% wt; pH 4.5 (◆) and pH 6.0 (□)) and the marketed amiodarone HCl formulation (Δ) at pH 3.9 and at 25° C. In this study, all three formulations were diluted with D5W. Unlike currently known formulations, the present formulation can be made approximately isotonic while still retaining an improved surface tension as compared to the CORDARONE® formulation. The present formulation can be made to have a tonicity between about 280 to 500 mOsm when the concentration of amiodarone is less than or equal to about 10 mg/mL.

As noted above, the molar ratio of amiodarone to SAE-CD affects the resulting clarity of solution. FIG. 9 depicts compositions for various solutions containing amiodarone HCl and SBE7-β-CD when prepared by a heating process, open symbols, or prepared at room temperature, solid symbols. The dashed-line indicates an approximate division between solutions that are dilutable and solutions that are not dilutable in solvents not containing added SAE-CD or other solubilizing agents. If the amiodarone concentration is excessively high with respect to SAE-CD, e.g., the molar ratio of amiodarone to SAE-CD is greater than about 0.91 or the molar ratio of SAE-CD to amiodarone is less than or equal to about 1.09±0.01, then the solution is typically not dilutable with D5W at room temperature. If the amiodarone concentration is such that the amiodarone to SAE-CD molar ratio is approximately equal to or less than 0.91 or the molar ratio of SAE-CD to amiodarone is greater than or equal to about 1.1±0.01, then the solutions will generally be dilutable with D5W at room temperature.

It should be understood that other SAE-CD compounds of the formula 1 may be used in the liquid formulation of the invention. These other SAE-CD formulations differ from SBE7-β-CD in their degree of substitution by sulfoalkyl groups, the number of carbons in the sulfoalkyl chain, their molecular weight, the number of glucopyranose units contained in the base cyclodextrin used to form the SAE-CD and or their substitution patterns. In addition, the derivatization of β-cyclodextrin with sulfoalkyl groups occurs in a controlled, although not exact manner. For this reason, the degree of substitution is actually a number representing the average number of sulfoalkyl groups per cyclodextrin (for example, SBE7-β-CD, has an average of 7 substitutions per cyclodextrin). In addition, the regiochemistry of substitution of the hydroxyl groups of the cyclodextrin is variable with regard to the substitution of specific hydroxyl groups of the hexose ring. For this reason, sulfoalkyl substitution of the different hydroxyl groups is likely to occur during manufacture of the SAE-CD, and a particular SAE-CD will possess a preferential, although not exclusive or specific, substitution pattern. Given the above, the molecular weight of a particular SAE-CD may vary from batch to batch and will vary from SAE-CD to SAE-CD. All of these variations can lead to changes in the complexation equilibrium constant $K_{1:1}$ which in turn will affect the required molar ratios of the SAE-CD to amiodarone. The equilibrium constant is also somewhat variable with temperature and allowances in the ratio are required such that the agent remains solubilized during the temperature fluctuations that can occur during manufacture, storage, transport, and use. The equilibrium constant is also variable with pH and allowances in the ratio are required such that the agent remains solubilized during pH fluctuations that can occur during manufacture, storage, transport, and use. The equilibrium constant is also variable by the presence of other excipients (e.g., buffers, preservatives, antioxidants) Accordingly, the ratio of SAE-CD/amiodarone may need to be varied (±from the ratios set forth herein in order to compensate for the above-mentioned variables.

The invention also provides a pharmaceutical kit comprising a first container containing a liquid vehicle and a second container containing a reconstitutable solid pharmaceutical composition as described above. The liquid vehicle comprises an aqueous liquid carrier such as water, dextrose, saline, lactated Ringer's solution, or any other pharmaceutically acceptable aqueous liquid vehicles for the preparation of a liquid pharmaceutical compound.

A complexation-enhancing agent can be added to the aqueous liquid formulation of the invention. A complexation-enhancing agent is a compound, or compounds, that enhance(s) the complexation of amiodarone with the SAE-CD. When the complexation-enhancing agent is present, the required ratio of SAE-CD to amiodarone may need to be changed such that less SAE-CD is required. Suitable complexation enhancing agents include one or more pharmacologically inert water soluble polymers, hydroxy acids, and other organic compounds typically used in liquid formulations to enhance the complexation of a particular agent with cyclodextrins. Suitable water soluble polymers include water soluble natural polymers, water soluble semisynthetic polymers (such as the water soluble derivatives of cellulose) and water soluble synthetic polymers. The natural polymers include polysaccharides such as inulin, pectins, algin derivatives and agar, and polypeptides such as casein and gelatin. The semisynthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose, hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Suitable hydroxy acids include by way of example, and without limitation, citric acid, malic acid, lactic acid, and tartaric acid and others known to those of ordinary skill in the art.

A solubility-enhancing agent can be added to the aqueous liquid formulation of the invention. A solubility-enhancing agent is a compound, or compounds, that enhance(s) the solubility of amiodarone in the liquid formulation. When a complexation-enhancing agent is present, the ratio of SAE-CD to amiodarone may need to be changed such that less SAE-CD is required. Suitable solubility enhancing agents include one or more organic solvents, detergents, soaps, surfactants and other organic compounds typically used in parenteral formulations to enhance the solubility of a particular agent. Suitable organic solvents include, for example, ethanol, glycerin, polyethylene glycols, propylene glycol, poloxomers, and others known to those of ordinary skill in the art.

Dosage levels of amiodarone adequate to suppress a life threatening arrhythmia, for both induction (for example, 150 mg over the first 10 minutes (15 mg/min) followed by 360 mg over the next 6 hours (1 mg/min)) and maintenance (for example, 540 mg over the remaining 18 hours (0.5 mg/min)) may be derived from the substantial literature on amiodarone, and in particular the package insert for the CORDARONE® product. Furthermore, the anesthetist and/or physician will be able modify the dose to achieve the desired effect in a patient in accordance with the conventional practices in the art.

It should be understood, that compounds used in the pharmaceutical arts generally serve a variety of functions or purposes. Thus, if a compound named herein is mentioned only once or is used to define more than one term herein, its purpose or function should not be construed as being limited solely to that named purpose(s) or function(s). Although not necessary, the formulation of the present invention may include a preservative, antioxidant, buffering agent, acidifying agent, alkalizing agent, antibacterial agent, antifungal agent, solubility-enhancing agent, complexation enhancing agent, solvent, electrolyte, salt, water, glucose, stabilizer, tonicity modifier, antifoaming agent, oil, bulking agent, cryoprotectant, or a combination thereof.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "antioxidant" is intended to mean an agent which inhibits oxidation and thus is used to prevent the deterioration of preparations by the oxidative process. Such compounds include by way of example and without limitation, acetone, sodium bisulfate, ascorbic acid, ascorbyl palmitate, citric acid, butylated hydroxyanisole, butylated hydroxytoluene, hydrophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, sodium metabisulfite, EDTA (edetate), pentetate and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, citric acid, maleic acid, monobasic sodium phosphate, dibasic sodium phosphate, lactic acid, tartaric acid, glycine, potassium metaphosphate, potassium phosphate, monobasic sodium acetate, sodium bicarbonate, sodium tartrate and sodium citrate anhydrous and dihydrate and others known to those of ordinary skill in the art.

As used herein, the term "stabilizer" is intended to mean a compound used to stabilize a therapeutic agent against physical, chemical, or biochemical process that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art. In one embodiment, the tonicity of the liquid formulation approximates that of the tonicity of blood or plasma.

As used herein, the term "antifoaming agent" is intended to mean a compound or compounds that prevents or reduces the amount of foaming that forms on the surface of the liquid formulation. Suitable antifoaming agents include by way of example and without limitation, dimethicone, simethicone, octoxynol and others known to those of ordinary skill in the art.

As used herein, the term "bulking agent" is intended to mean a compound used to add bulk to the reconstitutable solid and/or assist in the control of the properties of the formulation during preparation. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

As used herein, the term "solubilizing agent" is intended to mean a compound used to assist and or increase the solubility of a compound going into solution. Such compounds include, by way of example and without limitation, glycerin, glycerol, polyethylene glycol, propylene glycol and others known to those of ordinary skill in the art.

The formulation of the invention can also include water, glucose or saline and combinations thereof. In particular embodiments, the formulation includes water, saline, and glucose.

The chemical stability of the liquid formulations of the invention, in terms of a precipitate or gel forming, can be enhanced by adjusting the pH of the liquid carrier. The chemical stability can also be enhanced by converting the liquid formulation to a solid or powder formulation.

The pH of the liquid formulation will generally range from about pH 3.0 to about pH 7.0; however, liquid formulations having higher or lower pH values can also be prepared. It is contemplated that amiodarone stability can be increased by optimizing the pH as well as the SAE-CD to amiodarone concentration.

The liquid formulation of the invention can be provided in an ampoule, syringe, bottle, bag, vial or other such container typically used for parenteral formulations.

The liquid formulation of the invention can be prepared by numerous different methods. According to one method, a first aqueous solution comprising SAE-CD is prepared. Then, a second solution comprising an antiarrhythmic agent is prepared. Finally, the first and second solutions are mixed to form the liquid formulation. The first and second solutions can independently comprise other excipients and agents described herein. Additionally, the second solution can be water and/or an organic solvent-base solution. Another method of preparation is similar to the above-described method except that the antiarrhythmic agent is added directly to the first solution without the formation of a second solution. A third method of preparing the liquid formulation is similar to the above-described first method except that the SAE-CD is added directly to an aqueous second solution containing the antiarrhythmic agent without formation of the first solution. A fourth method of preparing the liquid formulation comprises the steps of adding an aqueous solution comprising an antiarrhythmic agent to a powdered or particulate SAE-CD and mixing the solution until the SAE-CD has dissolved. A fifth method of preparing the liquid formation comprises the steps of adding the antiarrhythmic agent directly to the powdered or particulate SAE-CD and then adding an aqueous solution and mixing until the SAE-CD and antiarrhythmic agent has dissolved. A sixth method for preparing the liquid formation comprises the steps of heating either the first solution or heating the second solution, or heating a combination thereof of any solutions described in the above methods followed by the step of cooling the respectively heated solution. A seventh method for preparing the liquid formation comprises the step of adjusting the pH of either the first solution or adjusting the pH of the second solution or adjusting the pH of a combination of either solutions described in any of the above methods. An eighth method comprises the steps of creating the liquid formulation by any of the above-described methods followed by the step of isolating a solid material by lyophilization, spray-drying, spray freeze-drying, vacuum-drying, antisolvent precipitation or a process utilizing a supercritical or near supercritical fluid. Any of the above solutions can contain other pharmaceutical excipients or ingredients as described herein.

Specific embodiments of the method of preparing the liquid formulation include those wherein the method further comprises the step of: 1) sterile filtering the formulation through a filtration medium wherein the pore size is about 0.22 $\mu$m or smaller; 2) sterilizing the liquid formulation by irradiation; 3) sterilizing the liquid formulation by treatment with ethylene oxide; 4) isolating a sterile powder from the sterilized liquid formulation; 5) purging the liquid with an inert gas to reduce the amount of dissolved oxygen in the liquid; and/or 6) one or more of the solutions used to prepare the liquid formulation is heated.

The first and second formulations can be mixed and formulated as a liquid dosage form prior to administration to a subject. Either one or both of the first and second pharmaceutical compositions can comprise additional pharmaceutical components.

The liquid formulation of the invention can be provided in a kit. The kit will comprise a first pharmaceutical composition comprising an SAE-CD and a second pharmaceutical composition comprising an antiarrhythmic agent. The first and second formulations can be mixed and formulated as a liquid dosage form prior to administration to a subject. Either one or both of the first and second pharmaceutical compositions can comprise additional pharmaceutical excipients. The kit is available in various forms.

In a first kit, the first and second pharmaceutical compositions are provided in separate containers or separate chambers of a container having two or more chambers. The first and second pharmaceutical compositions may be independently provided in either solid or powder or liquid form. For example, the SAE-CD can be provided in a reconstitutable powder form and the antiarrhythmic agent can be provided in powdered form. According to one embodiment, the kit would further comprise a pharmaceutically acceptable liquid carrier used to suspend and dissolve the first and/or second pharmaceutical compositions. Alternatively, a liquid carrier is independently included with the first and/or second pharmaceutical composition. The liquid carrier, however, can also be provided in a container or chamber separate from the first and second pharmaceutical compositions. As above, the first pharmaceutical composition, the second pharmaceutical composition and the liquid carrier can independently comprise a preservative, an antioxidant, a buffering agent, an acidifying agent, saline, glucose, an electrolyte, another therapeutic agent, an alkalizing agent, an antimicrobial agent, an antifungal agent, solubility enhancing agent or a combination thereof. The liquid formulation of the invention can be provided as a dosage form including a pre-filled vial, pre-filled bottle, pre-filled syringe, pre-filled ampoule, or plural ones thereof. Generally, a pre-filled container will contain at least a unit dosage form of the antiarrhythmic agent.

Specific embodiments of the kit include those wherein: 1) the first and second pharmaceutical compositions are contained in separate containers or separate chambers of a container having two or more chambers; 2) the kit further comprises a separate pharmaceutically acceptable liquid carrier; 3) a liquid carrier is included with the first and/or second pharmaceutical composition; 4) containers for the pharmaceutical compositions are independently selected at each occurrence from an evacuated container, a syringe, bag, pouch, ampule, vial, bottle, or any pharmaceutically acceptable device known to those skilled in the art for the delivery of liquid formulations; 5) the first pharmaceutical composition and/or second pharmaceutical composition and/or liquid carrier further comprises an antioxidant, a buffering agent, an acidifying agent, a solubilizing agent, a complexation enhancing agent, saline, dextrose, lyophilizing aids (for example, bulking agents or stabilizing agents), an electrolyte, another therapeutic agent, an alkalizing agent, an antimicrobial agent, an antifungal agent or a combination thereof; 6) the kit is provided chilled; 8) the liquid carrier and/or chamber has been purged with a pharmaceutically acceptable inert gas to remove substantially all of the oxygen dissolved in the liquid carrier; 9) the chambers are substantially free from oxygen; 10) the liquid carrier further comprises a buffering agent capable of maintaining a physiologically acceptable pH; 11) the chambers and solutions are sterile; 12) a diluent included in the kit comprises SAE-CD and is used to dilute a formulation that is non-dilutable in D5W at room temperature.

The term "unit dosage form" is used herein to mean a single or multiple dose form containing a quantity of the active ingredient and the diluent or carrier, said quantity being such that one or more predetermined units are normally required for a single therapeutic administration. In the case of multiple dose forms, such as liquid-filled ampoules, said predetermined unit will be one fraction such as a half or quarter of the multiple dose form. It will be understood that the specific dose level for any patient will depend upon a variety of factors including the indication being treated, therapeutic agent employed, the activity of therapeutic agent, severity of the indication, patient health, age, sex, weight, diet, and pharmacological response, the specific dosage form employed and other such factors.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" is taken to mean warm blooded animals such as mammals, for example, cats, dogs, mice, guinea pigs, horses, bovine cows, sheep, and humans.

The liquid formulation of the invention will comprise an effective amount of amiodarone. By the term "effective amount", it is understood that a therapeutically effective amount is contemplated. A therapeutically effective amount is the amount or quantity of amiodarone that is sufficient to elicit the required or desired therapeutic response, or in other words, the amount that is sufficient to elicit an appreciable biological response when administered to a subject.

As with other antiarrhythmic agents and formulations, the present formulation is used to suppress cardiac arrhythmias and/or life threatening arrhythmias. An arrhythmia is suppressed in a patient by administering a therapeutically effective initial dose of the antiarrhythmic agent followed by a maintenance dose over a period of time sufficient to suppress the arrhythmia. In general, the initial loading dose of an antiarrhythmic agent is accomplished by a first rapid infusion or injection of a therapeutically effective dose followed by a slow infusion or injection of a therapeutically effective dose depending on the needs of the individual patient. Maintenance of an antiarrhythmic actic with an antiarrhythmic agent is typically accomplished by administering to a patient by injection or infusion a lower amount of a therapeutically effective dose of the antiarrhythmic agent over a period of time depending upon the individual needs of the patient.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

Amiodarone HCl 50 mg/ml in a Solution Containing 25 mM Acetate Buffer, pH 4.5 and 30% w/v SBE7-β-CD.

| Ingredients | Amount |
| --- | --- |
| Amiodarone hydrochloride | 50 mg/mL |
| Sodium acetate trihydrate, USP | 3.4 mg/mL |
| Glacial acetic acid, USP | titrate to a pH of 4.5 |

| Ingredients | Amount |
| --- | --- |
| SBE7-β-CD | 300 mg/mL |
| Water | qs to 100 mL |

A solution was prepared by dissolving 340 mg sodium acetate and 30 g SBE7-β-CD in approximately 70 mL water. The pH was adjusted to 4.5 using glacial acetic acid. The solution was heated to 55° C. and while mixing, 5 g amiodarone HCL was added. Mixing was continued until the amiodarone was completely dissolved, then the solution was slowly cooled to room temperature. The solution was brought to a final volume of 100 mL with water, to give a visibly clear and dilutable solution. The solution was sterilized by filtration through a 0.22-micrometer filter (Polyvinylidene fluoride Durapore hydrophilic membrane). This example demonstrates preparation of a solution according to the invention at pH 4.5.

EXAMPLE 2
The Procedure of Example 1 was Followed Except the pH was Adjusted to 3.5

EXAMPLE 3
Amiodarone HCL 50 mg/ml in a Solution Containing Glycerin 20% w/v, SBE7-β-CD 30% w/v and Disodium EDTA 0.1% w/v.

| Ingredients | Amount |
| --- | --- |
| Amiodarone hydrochloride | 50 mg/mL |
| Disodium EDTA, USP | 1.0 mg/mL |
| Glycerin, USP | 200 mg/mL |
| SBE7-β-CD | 300 mg/mL |
| Water | qs 100 mL |

A solution was prepared by dissolving 100 mg disodium EDTA and 30 g SBE7-β-CD in approximately 50 mL water. Glycerin (20 g) was added with mixing and the solution was heated to 75° C. While mixing, 5 g amiodarone HCL was added, and mixing was continued until it was completely dissolved. The solution was slowly cooled to room temperature and then brought to 100 ml final volume with water. The resulting solution was visibly clear and dilutable with a pH of 4.8. The solution was sterilized by filtration through a 0.22-micrometer filter (Polyvinylidene fluoride Durapore hydrophilic membrane). Accordingly, a formulation according to the invention can include an organic solvent and an antioxidant.

EXAMPLE 4
Amiodarone HCL 50 mg/ml in a Solution Containing 80 mM Acetate Buffer, pH 5.0 and 30% w/v SBE7-β-CD

| Ingredients | Amount |
| --- | --- |
| Amiodarone hydrochloride | 50 mg/mL |
| Sodium acetate trihydrate, USP | 10.9 mg/mL |
| Glacial acetic acid, USP | titrate to a pH of 5.0 |
| SBE7-β-CD | 300 mg/mL |
| Water | qs to 10 ml |

Sodium acetate (109 mg) and SBE7-β-CD (3 g) were dissolved in approximately 7 mL water. The solution pH was adjusted to 5.0 using glacial acetic acid then the solution was heated to 55° C. Five hundred milligrams of amiodarone HCL were added to the solution with mixing. The mixing was continued until the amiodarone was completely dissolved. The solution was slowly cooled to room temperature then brought to volume (10 mL) with water. The resulting solution was visibly clear and dilutable. Accordingly, a formulation according to the invention can comprise acetate buffer and can be prepared at a pH of about 5.

EXAMPLE 5
Amiodarone HCL 50 mg/ml in 80 mM Sodium Acetate and 30% w/v SBE7-β-CD.

| Ingredient | | Amount |
| --- | --- | --- |
| Solution A | SBE7-β-CD | 1.50 g |
| | Water | q.s. |
| | Sodium acetate trihydrate | 54.5 mg |
| | Glacial acetic acid | titrate to pH 4.5 |
| Solution B | Amiodarone HCl | 250 mg |
| | Methanol | 2.5 mL |

Solution A was prepared by dissolving 1.5 g SBE7-β-CD, and 54.5 mg sodium acetate in sufficient water to obtain a solution containing 30% w/v SBE7-β-CD. The pH of the solution was adjusted to 4.5 with glacial acetic acid. Solution B was prepared by dissolving 250 mg amiodarone HCl in 2.5 mL methanol. Solution A was heated to 55° C. and solution B was added to solution A with gentle stirring. The solution was held at 55° C. until the methanol was removed by evaporation. The solution was cooled to room temperature resulting in a visibly clear solution that was dilutable. Accordingly, a formulation according to the invention can comprise an organic solvent and a buffering agent.

EXAMPLE 6
Amiodarone HCL 50 mg/ml in 80 mM Acetate Buffer, pH 5.0, 0.1% Disodium EDTA and 30% w/v SBE7-β-CD.

| Ingredients | Amount |
| --- | --- |
| Amiodarone hydrochloride | 50 mg/mL |
| Sodium acetate trihydrate, USP | 10.9 mg/mL |
| Glacial acetic acid, USP | titrate to a pH of 5.0 |
| Disodium EDTA, USP | 1.0 mg/mL |
| SBE7-β-CD | 300 mg/mL |
| Water | qs to 5.0 ml |

A solution was prepared by dissolving 54.5 mg sodium acetate, 5 mg disodium EDTA and 1.5 g SBE7-β-CD in approximately 4 mL water. The pH was adjusted to 5.0 using glacial acetic acid. The solution was heated to 55° C. and 250 mg amiodarone HCL was added with mixing. Mixing was continued until the amiodarone was completely dissolved. The solution was slowly cooled to room temperature and water was added to bring the final volume to 5 mL. The solution was visibly clear.

EXAMPLE 7
Amiodarone HCL 50 mg/ml in a Solution Containing 25 mM Citrate Buffer, pH 4.0 and 20% w/v SBE7-β-CD.

| Ingredients | Amount |
| --- | --- |
| Amiodarone hydrochloride | 50 mg/mL |
| Citric acid, momohydrate, USP | 3.22 mg/mL |

-continued

| Ingredients | Amount |
| --- | --- |
| Sodium acetate dihydrate, USP | 3.02 mg/mL |
| SBE7-β-CD | 200 mg/mL |
| Water | qs to 50 mL |

A solution was prepared by dissolving 161 mg citric acid, 151 mg sodium citrate and 10 g SBE7-β-CD in approximately 35 mL water. The solution was heated to 55° C. and 2.5 g amiodarone HCL was added with mixing. Mixing was continued until the amiodarone was completely dissolved, then the solution was slowly cooled to room temperature. The solution was brought to final volume (50 mL) with water. The resulting solution was visibly clear and dilutable. The solution was sterilized by filtration through a 0.22-micrometer filter (Polyvinylidene fluoride Durapore hydrophilic membrane). Accordingly, a solution according to the invention can comprise low concentrations of an SAE-CD, e.g., 20% wt.

EXAMPLE 8

Amiodarone HCL 50 mg/ml in 100 mM Citrate Buffer, pH 4.5 with 30% w/v SBE7-β-CD

| Ingredients | Amount |
| --- | --- |
| Amiodarone hydrochloride | 50 mg/mL |
| Citric acid, monohydrate, USP | 9.66 mg/mL |
| Sodium citrate, dihydrate, USP | 15.8 mg/mL |
| SBE7-β-CD | 300 mg/mL |
| Water | qs to 10 ml |

A solution was prepared by dissolving 96.6 mg citric acid, 158 mg sodium citrate and 3 g SBE7-β-CD in approximately 7 mL water. The solution was heated to 55° C., and 500 mg amiodarone HCL was added with mixing. Mixing was continued until the amiodarone was completely dissolved. The solution was then slowly cooled to room temperature and water was added to bring the volume to 10 mL. The resulting solution had a pH value of 4.5 and was visibly clear and dilutable. Accordingly, a formulation according to the invention can comprise higher concentrations, e.g., 100 mM, of buffer, especially citrate buffer, than can prior art formulations.

EXAMPLE 9

The pH of the solution obtained in example 8 was adjusted to a pH of approximately 5.5 using 1N sodium hydroxide solution. A visibly clear solution was produced. Accordingly, a liquid formulation according to the invention can be prepared at a pH approximating the pKa of amiodarone.

EXAMPLE 10

Amiodarone HCL 50 mg/ml in a Solution Containing 114 mM Monobasic Sodium Phosphate and 30% w/v SBE7-β-CD.

| Ingredients | Amount |
| --- | --- |
| Amiodarone hydrochloride | 50 mg |
| Sodium phosphate monobasic, USP | 15.96 mg |

-continued

| Ingredients | Amount |
| --- | --- |
| SBE7-β-CD | 300 mg |
| Water | qs to 1.0 ml |

A solution was prepared by dissolving sodium phosphate monobasic and SBE7-β-CD in water. The solution was heated to 75° C. and while mixing amiodarone HCL was added. Mixing was continued until the amiodarone was completely dissolved, then the solution was slowly cooled to room temperature. The solution (pH 4.5) was brought to volume with water to yield a visibly clear solution. The pH of the solution is adjusted to 5.5 using 1N sodium hydroxide solution. A visibly clear solution was produced that was dilutable. Accordingly, a formulation according to the invention can comprise phosphate buffer at a pH approximating the pKa of amiodarone. Moreover, a formulation according to the invention can be prepared at elevated temperature, e.g., about 75° C.

EXAMPLE 11

Solid Formulation for Reconstitution to Give a Solution Containing 50 mL Amiodarone HCl and 300 mg/mL SBE7-β-CD.

A solution was prepared in water containing 7.5 g SBE7-β-CD and 1.25 g amiodarone HCl in a total volume of 25 mL. The pH of the solution was adjusted to 4.5 with concentrated HCl or 10 N NaOH. The solution was filtered through a 0.22 micron filter and 3 mL aliquots were filled into vials and lyophilized to give solid formulations. The contents of a vial were reconstituted with 3 mL water to give a clear solution. Accordingly, a liquid formulation made according to the invention can be converted to a reconstitutable solid formulation according to the invention by removal of most of the water from the liquid formulation.

EXAMPLE 12

Amiodarone 50 mg/ml in 50 mM Citrate Buffer, pH ~4.5, and Sulfobutyl Ether 4-β-cyclodextrin (SBE4-β-CD).

A 3.8 mL aliquot of a solution containing 4.4 mL citric acid (50 mM) and 4.6 mL sodium citrate (50 mM) was mixed with 1200 mg of sulfobutyl ether β-cyclodextrin, degree of substitution ~4 (SBE4-β-CD) until dissolved. The solution was heated to 55° C. and 200 mg amiodarone HCl were added with mixing until dissolved. The solution was slowly cooled to room temperature and yielded a clear solution. Accordingly, a formulation according to the invention can comprise an SBE4-β-CD while maintaining an SAE-CD to amiodarone mole ratio ≧1.1±0.01.

EXAMPLE 13

Amiodarone HCl (50 mg (0.73 mM)) and SBE7-β-CD (335 mg; 1.54 mM) were combined and dissolved in a total volume of 100 mL water. The resulting clear solution was dried under vacuum. A 50 mg aliquot of the dry product was dissolved in 25 mL 60 mM phosphate buffer, pH 7, resulting in a clear solution. Accordingly, unlike the prior art, a reconstitutable powder containing SAE-CD and phosphate buffer can be made.

EXAMPLE 14
Amiodarone HCL 50 mg/ml in a Solution Containing 25 mM Citrate Buffer, pH 4.0 and 15% w/v SBE7-β-CD

| Ingredients | Amount |
| --- | --- |
| Amiodarone hydrochloride | 50 mg/mL |
| Citric acid, monohydrate, USP | 3.22 mg/mL |
| Sodium citrate, dihydrate, USP | 3.02 mg/mL |
| SBE7-β-CD | 150 mg/mL |
| Water | qs to 10 mL |

A solution was prepared by dissolving 32.2 mg citric acid, 30.2 mg sodium citrate and 1.5 g SBE7-β-CD in approximately 7 mL water. The solution was heated to 55° C. and 500 mg amiodarone HCL was added with mixing. Mixing was continued until the amiodarone was completely dissolved, then the solution was slowly cooled to room temperature. The solution was brought to final volume (10 mL) with water. The resulting solution was visibly clear. The solution was sterilized by filtration through a 0.22-micrometer filter (Polyvinylidene fluoride Durapore hydrophilic membrane). Dilution to 1.5 mg/mL amiodarone in an aqueous 5% dextrose solution produced a hazy solution. Accordingly, the a formulation according to the invention can be made clear while having an SAE-CD to amiodarone mole ratio of $\leq 1.09 \pm 0.01$ and while being not dilutable with an aqueous liquid (not comprising a solubilizing agent) at room temperature. Moreover, a clear formulation comprising a low concentration of SAE-CD, e.g., about 15% wt., can be made.

EXAMPLE 15
Amiodarone HCL 68.2 mg/ml in a Solution Containing 25 mM Citrate Buffer, pH 3.5 and 23% w/v SBE7-β-CD

| Ingredients | Amount |
| --- | --- |
| Amiodarone hydrochloride | 68.2 mg/mL |
| Citric acid, monohydrate, USP | 4.22 mg/mL |
| Sodium citrate, dihydrate, USP | 2.41 mg/mL |
| SBE7-β-CD | 230 mg/mL |
| Water | qs to ~4.5 mL |

A solution was prepared by dissolving 18.9 mg citric acid, 10.8 mg sodium citrate and 1.0 g SBE7-β-CD in approximately 4 mL water. The solution was heated to 55° C. and 305 mg amiodarone HCL was added with mixing. Mixing was continued until the amiodarone was completely dissolved, then the solution was slowly cooled to room temperature. The solution was brought to final volume (~4.5 mL) with water. The resulting solution was visibly clear and had a SBE/Amiodarone mole ratio of 1.02. The solution was sterilized by filtration through a 0.22-micrometer filter (Polyvinylidene fluoride Durapore hydrophilic membrane). Dilution to 1.5 mg/mL amiodarone in a 5% dextrose solution produced a hazy solution. The formulation was diluted to 1.5 mg/mL amiodarone in an aqueous 5% dextrose solution containing 0.37 mM SBE7-β-CD to produce a visibly clear solution (final SBE/amiodarone mol ratio 1.19). Accordingly, a liquid formulation that is non-dilutable with water or aqueous 5% dextrose solution at about 25° C. or at room temperature can be rendered dilutable at room temperature by using an aqueous diluent comprising SAE-CD as long as the final mole ratio of SAE-CD to amiodarone is $\geq$ about 1.1.

Clarity of the solutions herein was determined by visual inspection; however, other known methods for determining the clarity of a solution can be performed. Exemplary other methods include transmittance spectrophotometry at a wavelength of 800 nm. Using either method, solutions prepared according to the invention were determined to be at least visually clear. A clear liquid will generally contain no precipitate or may contain precipitate present in an amount of less than or equal to about 3% wt. of the amiodarone or acid-ionizable active agent.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except by the appended claims. All of the embodiments disclosed and claimed herein can be made and executed without undue experimentation in light of the present disclosure.

We claim:

1. A water dilutable clear liquid formulation comprising amiodarone and a sulfoalkyl ether cyclodextrin (SAE-CD), wherein the molar ratio of SAE-CD to amiodarone is greater than or equal to about $1.1 \pm 0.01$, and the liquid formulation is dilutable with water at ambient temperature without significant precipitation of amiodarone and without the need of surfactant, organic solvent, soap or detergent, and wherein the SAE-CD is a compound or mixture of compounds of the Formula 1

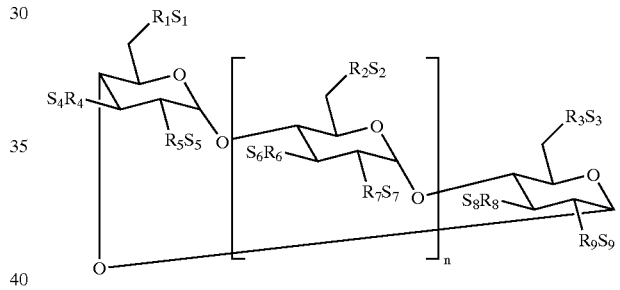

Formula 1 wherein: n is 5, or 6;
$R_1$, $R_2$, $R_3$, $R_4$, $R_5$, $R_6$, $R_7$, $R_8$, and $R_9$ are each, independently, —O— or a —O—$(C_2$-$C_6$ alkylene)-$SO_3^-$ group, wherein at least one of $R_1$ and $R_2$ is independently a —O—$(C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a pharmaceutically acceptable cation.

2. The formulation of claim 1, wherein the amiodarone concentration is in the range of less than or equal to about 3 mg/ml, the SAE-CD concentration is less than or equal to about 0.9% wt., and the pH of the liquid approximates or is less than the pKa of amiodarone.

3. The formulation of claim 1, wherein the amiodarone concentration is greater than or equal to about 34 mg/mL, the SAE-CD concentration is greater than or equal to about 55 mM, and the pH of the liquid approximates or is less than the pKa of amiodarone.

4. The formulation of claim 1, wherein the compound of Formula 1 has an average degree of substitution of about 4 or 7.

5. The formulation of claim 1 further comprising a solubilizing agent, antioxidant, buffering agent, acidifying agent, complexation enhancing agent, saline, dextrose, lyophilizing aid, bulking agent, stabilizing agents, electrolyte, another therapeutic agent, alkalizing agent, antimicrobial agent, antifungal agent or a combination thereof.

6. The formulation of claim 5, wherein the buffering agent is an organic or inorganic acid, organic or inorganic base, or salt thereof.

7. The formulation of claim 6, wherein the buffering agent is selected from the group consisting of acetic acid, citric acid, phosphoric acid, boric acid, or a salt thereof.

8. The formulation of claim 5, wherein the total ionic strength of charged species in solution, excluding amiodarone and SAE-CD, is less than about 0.5 M.

9. The formulation of claim 1, wherein the formulation has a surface tension greater than about 50 dynes/cm when the concentration of amiodarone is less than or equal to about 10 mg/mL.

10. The formulation of claim 1, wherein the formulation has a tonicity between about 280 to 500 mOsm when the concentration of amiodarone is less than or equal to about 10 mg/mL.

11. A water dilutable clear liquid formulation comprising amiodarone and an SAE-CD, wherein
    a. the molar ratio of SAE-CD to amiodarone is greater than or equal to about 1.1±0.01;
    b. the liquid formulation is dilutable with water at ambient temperature without significant precipitation of amiodarone and without the need of surfactant, organic solvent, soap or detergent;
    c. the amiodarone concentration is in the range of less than or equal to about 3 mg/ml;
    d. the SAE-CD concentration is less than or equal to about 4.5 mM;
    e. the pH of the liquid approximates or is less than the pKa of amiodarone; and
    f. the sulfoalkyl ether cyclodextrin is a compound or mixture of compounds of the Formula 1

Formula 1

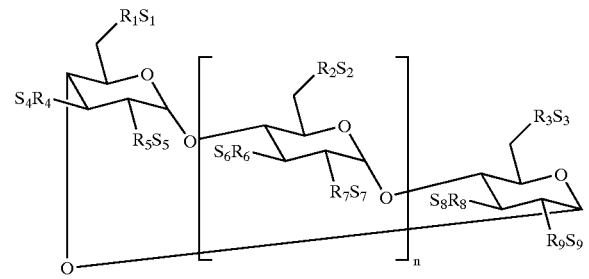

wherein: n is 5, or 6;

$R_1$, $R_2$, $R_3$, $R_4$, $R_5$, $R_6$, $R_7$, $R_8$, and $R_9$ are each, independently, —O— or a —O—$(C_2$-$C_6$ alkylene)-$SO_3^-$ group, wherein at least one of $R_1$ and $R_2$ is independently a —O—$(C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a pharmaceutically acceptable cation.

12. The formulation of claim 11, wherein the compound of Formula 1 has an average degree of substitution of about 4 or 7.

13. The formulation of claim 11, wherein the total ionic strength of charged species in solution, excluding amiodarone and SAE-CD, is less than about 0.5 M.

14. The formulation of claim 11, wherein the formulation has a surface tension greater than about 50 dynes/cm and a tonicity between about 280 to 500 mOsm.

15. A water dilutable clear liquid formulation comprising water, amiodarone and an SAE-CD, wherein a. the molar ratio of SAE-CD to amiodarone is greater than or equal to about 1.1±0.01;
    b. the liquid formulation is dilutable with water at ambient temperature without significant precipitation of amiodarone and without the need of surfactant, organic solvent, soap or detergent;
    c. the amiodarone concentration is greater than or equal to about 50 mM;
    d. the SAE-CD concentration is greater than or equal to about 55 mM;
    e. the pH of the liquid medium approximates or is less than the pKa of amiodarone; and
    f. the sulfoalkyl ether cyclodextrin is a compound or mixture of compounds of the Formula 1

Formula 1

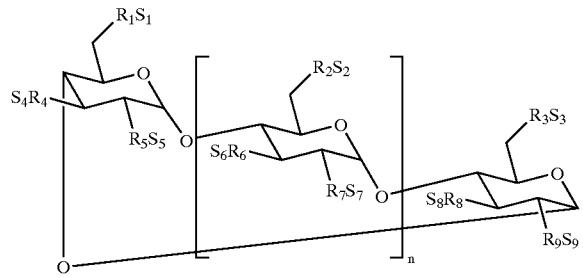

wherein: n is 5, or 6;

$R_1$, $R_2$, $R_3$, $R_4$, $R_5$, $R_6$, $R_7$, $R_8$, and $R_9$ are each, independently, —O— or a —O—$(C_2$-$C_6$ alkylene)-$SO_3^-$ group, wherein at least one of $R_1$ and $R_2$ is independently a —O—$(C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a pharmaceutically acceptable cation.

16. The formulation of claim 15, wherein the compound of Formula 1 has an average degree of substitution of about 4 or 7.

17. A clear liquid formulation comprising amiodarone, SAE-CD and an aqueous liquid carrier, wherein the molar ratio of SAE-CD to amiodarone is less than or equal to about 1.09±0.01 and greater than or equal to about 0.3; the pH of the liquid formulation approximates or is less than the pKa of amiodarone; the liquid formulation has been exposed to a temperature of greater than or equal to about 45° C. thereby rendering the liquid formulation clear; and wherein the SAE-CD is a compound or mixture of compounds of the Formula 1

Formula 1

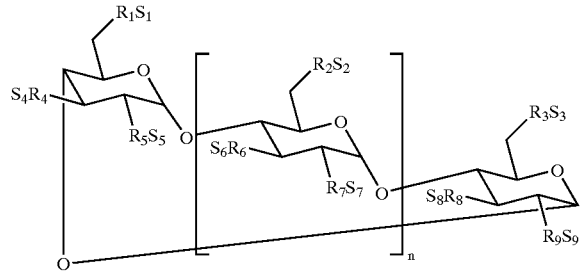

wherein: n is 4, 5, or 6;

$R_1$, $R_2$, $R_3$, $R_4$, $R_5$, $R_6$, $R_7$, $R_8$, and $R_9$ are each, independently, —O— or a —O—$(C_2$-$C_6$ alkylene)-

SO$_3^-$ group, wherein at least one of R$_1$ and R$_2$ is independently a —O—(C$_2$-C$_6$ alkylene)-SO$_3^-$ group; and S$_1$, S$_2$, S$_3$, S$_4$, S$_5$, S$_6$, S$_7$, S$_8$, and S$_9$ are each, independently, a pharmaceutically acceptable cation.

18. The formulation of claim 17, wherein the liquid formulation is dilutable with a heated pharmaceutically acceptable aqueous liquid carrier, an aqueous liquid comprising SAE-CD or an aqueous liquid comprising a solubilizing agent, soap, detergent, surfactant, or complexation enhancing agent to form a clear diluted liquid formulation.

19. A clear water dilutable concentrated liquid formulation comprising SBE7-β-CD and amiodarone, wherein the amiodarone is present in an amount of greater than about 2 mg/mL, and the SBE7-β-CD to amiodarone ratio is greater than or equal to about 1.1±0.01, wherein the liquid formulation can be diluted with water at about 20° C. to 30° C. to form a clear diluted liquid formulation.

20. A clear ready-to-inject sterile liquid formulation comprising SBE7-β-CD and amiodarone, wherein the SBE7-β-CD is present in an amount of at least about 0.3% wt. and the amiodarone is present in amount of 1–2 mg/mL.

21. A clear water dilutable concentrated aqueous liquid formulation comprising a pharmaceutically acceptable aqueous liquid, SAE-CD and amiodarone, wherein the amiodarone is present in an amount of greater than about 2 mg/mL; the SAE-CD to amiodarone ratio is greater than or equal to about 1.1±0.01; the SAE-CD is a compound or mixture of compounds of the Formula 1

Formula 1

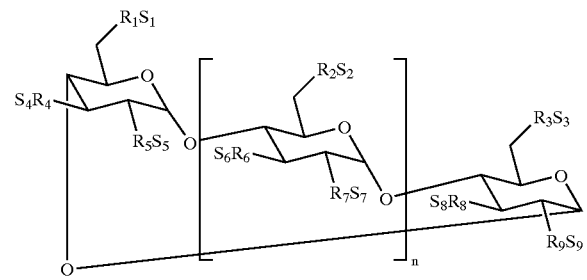

wherein: n is 5, or 6;

R$_1$, R$_2$, R$_3$, R$_4$, R$_5$, R$_6$, R$_7$, R$_8$, and R$_9$ are each, independently, —O— or a —O—(C$_2$-C$_6$ alkylene)-SO$_3^-$ group, wherein at least one of R$_1$ and R$_2$ is independently a —O—(C$_2$-C$_6$ alkylene)-SO$_3^-$ group; and S$_1$, S$_2$, S$_3$, S$_4$, S$_5$, S$_6$, S$_7$, S$_8$, and S$_9$ are each, independently, a pharmaceutically acceptable cation; and the liquid formulation can be diluted with water at about 20° C. to 30° C. to form a clear diluted liquid formulation.

22. A clear ready-to-inject sterile aqueous liquid formulation comprising pharmaceutically acceptable aqueous liquid, SAE-CD and amiodarone, wherein the SAE-CD is present in an amount of at least about 0.3% wt.; amiodarone is present in an amount of about 0.482 to 100.8 mg/ml; the SAE-CD is a compound or mixture of compounds of the Formula 1

Formula 1

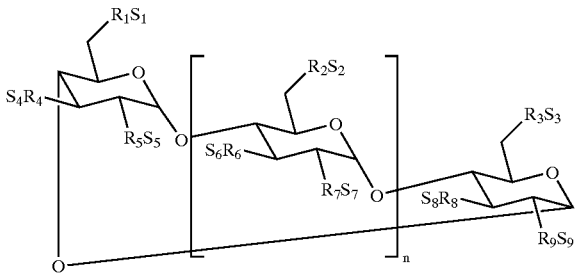

wherein: n is 4, 5, or 6;

R$_1$, R$_2$, R$_3$, R$_4$, R$_5$, R$_6$, R$_7$, R$_8$, and R$_9$ are each, independently, —O— or a —O—(C$_2$-C$_6$ alkylene)-SO$_3^-$ group, wherein at least one of R$_1$ and R$_2$ is independently a —O—(C$_2$-C$_6$ alkylene)-SO$_3^-$ group; and S$_1$, S$_2$, S$_3$, S$_4$, S$_5$, S$_6$, S$_7$, S$_8$, and S$_9$ are each, independently, a pharmaceutically acceptable cation.

23. A clear ready-to-inject sterile aqueous liquid comprising pharmaceutically acceptable aqueous liquid, SAE-CD and amiodarone, wherein SAE-CD is present in an amount of less than or equal to about 0.055 M; amiodarone is present in an amount of less than or equal to about 0.05 M; the molar ratio of SAE-CD amiodarone is less than or equal to about 1.09±0.01 and greater than or equal to about 0.3; and SAE-CD is a compound or mixture of compounds of the Formula 1

Formula 1

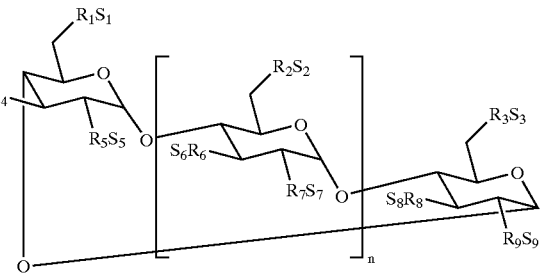

wherein: n is 4, 5, or 6;

R$_1$, R$_2$, R$_3$, R$_4$, R$_5$, R$_6$, R$_7$, R$_8$, and R$_9$ are each, independently, —O— or a —O—(C$_2$-C$_6$ alkylene)-SO$_3^-$ group, wherein at least one of R$_1$ and R$_2$ is independently a —O—(C$_2$-C$_6$ alkylene)-SO$_3^-$ group; and S$_1$, S$_2$, S$_3$, S$_4$, S$_5$, S$_6$, S$_7$, S$_8$, and S$_9$ are each, independently, a pharmaceutically acceptable cation.

24. The liquid formulation of claim 23, wherein the liquid formulation has been prepared by heating the pharmaceutically acceptable aqueous liquid and/or the liquid formulation at a temperature of at least about 30° C.

25. The liquid formulation of claim 23, wherein the liquid formulation has been prepared by heating the pharmaceutically acceptable aqueous liquid and/or the liquid formulation at a temperature of at least about 30° C.

26. The liquid formulation of claim 15, wherein the liquid formulation has been prepared by heating the pharmaceutically acceptable aqueous liquid and/or the liquid formulation at a temperature of at least about 30° C.

27. A water dilutable clear aqueous liquid formulation comprising water, amiodarone and an SAE-CD, wherein
   a. the molar ratio of SAE-CD to amiodarone is greater than or equal to about 1.1±0.01;
   b. the liquid formulation is dilutable with water at ambient temperature without significant precipitation of amiodarone and without the need of surfactant, organic solvent, soap or detergent;
   c. the amiodarone concentration is less than or equal to about 50 mM;
   d. the pH of the liquid medium approximates or is less than the pKa of amiodarone; and
   e. the sulfoalkyl ether cyclodextrin is a compound or mixture of compounds of the Formula 1

Formula 1

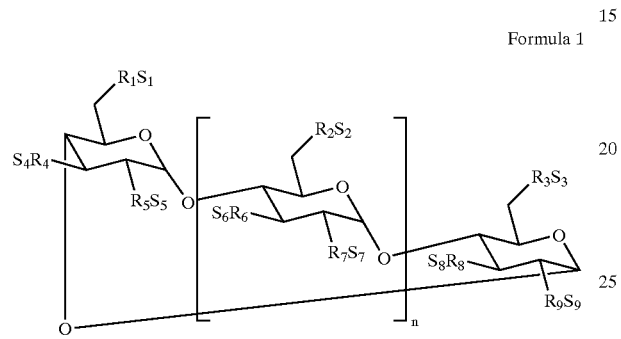

wherein: n is 4, 5, or 6;
$R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and
$S_1$, $S_2$, $S_3$, $S_4$, $S_5$, $S_6$, $S_7$, $S_8$, and $S_9$ are each, independently, a pharmaceutically acceptable cation.

28. The formulation of claim 27, wherein the SAE-CD concentration is less than or equal to about 55 mM.

29. A method of preparing a clear liquid formulation comprising the steps of:
   a. providing amiodarone, SAE-CD and a pharmaceutically acceptable aqueous liquid carrier to form a mixture, wherein the molar ratio of SAE-CD to amiodarone is less than about 1.09±0.1 and greater than or equal to about 0.3; and
   b. heating the liquid carrier and/or liquid formulation at a temperature of at least about 45° C. thereby forming the clear liquid formulation; wherein SAE-CD is a compound or mixture of compounds of the Formula 1

Formula 1

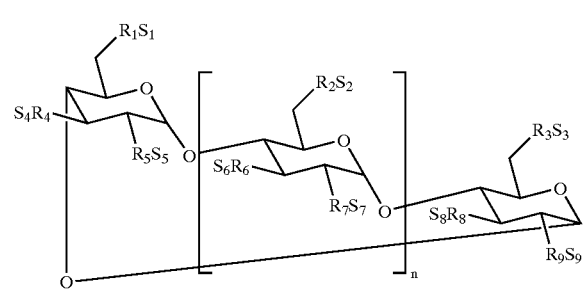

wherein: n is 4, 5, or 6;
$R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group, wherein at least one of $R_1$ and $R_2$ is independently a —O—($C_2$-$C_6$ alkylene)-$SO_3^-$ group; and
$S_1$, $S_2$, $S_3$, $S_4$, $S_5$, $S_6$, $S_7$, $S_8$, and $S_9$ are each, independently, a pharmaceutically acceptable cation.

* * * * *